US009949892B2

(12) United States Patent
Xu et al.

(10) Patent No.: US 9,949,892 B2
(45) Date of Patent: Apr. 24, 2018

(54) PULSE OXIMETRY-BASED CARDIO-PULMONARY RESUSCITATION (CPR) QUALITY FEEDBACK SYSTEMS AND METHODS

(71) Applicants: Peking Union Medical College Hospital, Chinese Academy of Medical Sciences, Beijing (CN); SHENZHEN MINDRAY BIO-MEDICAL ELECTRONICS CO., LTD., Shenzhen (CN)

(72) Inventors: Jun Xu, Beijing (CN); Xuezhong Yu, Beijing (CN); Fei Han, Shenzhen (CN); Liangliang Zheng, Beijing (CN); Huadong Zhu, Beijing (CN); Cheng Wang, Shenzhen (CN); Xiaocui Zhang, Shenzhen (CN); Chen Li, Beijing (CN); Jingming Yang, Shenzhen (CN); Xingliang Jin, Shenzhen (CN)

(73) Assignees: PEKING UNION MEDICAL COLLEGE HOSPITAL, Beijing (CN); SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 551 days.

(21) Appl. No.: 14/497,209

(22) Filed: Sep. 25, 2014

(65) Prior Publication Data
US 2015/0105637 A1 Apr. 16, 2015

(30) Foreign Application Priority Data

Oct. 11, 2013 (CN) .......................... 2013 1 0474008
May 16, 2014 (CN) .......................... 2014 1 0208903

(51) Int. Cl.
A61B 5/1455 (2006.01)
A61B 5/02 (2006.01)
(Continued)

(52) U.S. Cl.
CPC ......... *A61H 31/005* (2013.01); *A61B 5/0205* (2013.01); *A61B 5/02416* (2013.01);
(Continued)

(58) Field of Classification Search
CPC ................ A61H 31/005; A61B 5/1455; A61B 5/14551; A61B 5/14552; A61B 5/0205; A61B 5/7282
See application file for complete search history.

(56) References Cited

U.S. PATENT DOCUMENTS

2001/0047140 A1* 11/2001 Freeman .............. A61H 31/005
601/41
2004/0267324 A1 12/2004 Geheb et al.
(Continued)

FOREIGN PATENT DOCUMENTS

EP 2497417 A1 9/2012

OTHER PUBLICATIONS

Wijshoff et al., Detection of a Spontaneous Pulse in Photoplethysmograms During Automated Cardiopulmonary Resuscitation in a Porcine Model, Resuscitation 84, Jul. 23, 2013, pp. 1625-1632, Elsevier Ireland Ltd., Ireland.
(Continued)

*Primary Examiner* — Eric Winakur
(74) *Attorney, Agent, or Firm* — Kory D. Christensen; Polsinelli LLP

(57) ABSTRACT

Medical devices, plug-ins, systems, and methods for CPR quality feedback are disclosed. The medical devices can calculate peripheral circulation relevant parameters based on measured signals containing at least partial hemodynamic
(Continued)

characteristics. Amplitude and area characteristics included in the peripheral circulation relevant parameters can further be determined for providing feedback and control relating to CPR quality during the compression process. Also, compression interruption during CPR can be evaluated based on a pulse waveform generated from the measured signals.

25 Claims, 19 Drawing Sheets

(51) Int. Cl.
A61H 31/00 (2006.01)
A61B 5/0205 (2006.01)
A61B 5/024 (2006.01)
A61B 5/00 (2006.01)
A61N 1/39 (2006.01)

(52) U.S. Cl.
CPC ...... A61B 5/14551 (2013.01); A61B 5/14552 (2013.01); A61B 5/486 (2013.01); A61B 5/4836 (2013.01); A61B 5/4848 (2013.01); A61B 5/6826 (2013.01); A61B 5/7278 (2013.01); A61B 5/7282 (2013.01); A61B 5/743 (2013.01); A61H 31/006 (2013.01); A61H 31/007 (2013.01); A61B 5/02405 (2013.01); A61B 5/02427 (2013.01); A61H 2201/501 (2013.01); A61H 2201/5043 (2013.01); A61H 2201/5097 (2013.01); A61H 2230/04 (2013.01); A61H 2230/06 (2013.01); A61H 2230/065 (2013.01); A61H 2230/207 (2013.01); A61H 2230/208 (2013.01); A61N 1/3925 (2013.01)

(56) References Cited

U.S. PATENT DOCUMENTS

| | | | |
|---|---|---|---|
| 2006/0149144 | A1 | 7/2006 | Lynn et al. |
| 2008/0171311 | A1* | 7/2008 | Centen ............... A61H 31/005 601/41 |
| 2014/0058233 | A1* | 2/2014 | Koyama ............ A61B 5/14535 600/328 |
| 2015/0105636 | A1* | 4/2015 | Hayman ............ A61B 5/14552 600/323 |

OTHER PUBLICATIONS

Wijshoff et al., Potential of Photoplethysmography to Guide Pulse Checks During Cardiopulmonary Resuscitation: Observations in an Animal Study, Resuscitation 2013, ERC Symposium on Outcomes Abstract of Oral and Poster Presentations, Oral Presentations, 2013, Elsevier.
Meaney, et al., "Cardiopulmonary Resuscitation Quality: Improving Cardiac Resuscitation Outcomes Both Inside and Outside the Hospital: A Consensus Statement from the American Heart Association," Circulation, Jun. 25, 2013, pp. 417-435, vol. 128, American Heart Association, Inc., Dallas, TX.
Berg, et al., "Adverse Hemodynamic Effects of Interrupting Chest Compressions for Rescue Breathing During Cardiopulmonary Resuscitation for Ventricular Fibrillation Cardiac Arrest," Circulation, Nov. 13, 2001, pp. 2465-2470, vol. 104, American Heart Association, Inc., Dallas, TX.
Reuven, et al., "Arterial and Plethsmographic Waveform Analysis in Anesthetized Patients with Hypovolemia," Anesthesiology, Jul. 2010, pgs. 83-91, vol. 113. (1), American Society of Anesthesiologists, Inc.
Abella, et al., "Chest Compression Rates During Cardiopulmonary Resuscitation Are Suboptimal: A Prospective Study During In-Hospital Cardiac Arrest," Circulation, Feb. 1, 2005, pp. 428-434, vol. 111(4), American Heart Association, Inc., Dallas, TX.
Perkins, et al., "Compression feedback devices over estimate chest compression depth when performed on a bed," Resuscitation, 2009, pp. 79-82, vol. 80, Elsevier Ireland Ltd.
Reynolds, et al., "Coronary Perfusion Pressure and Return of Spontaneous Circulation After Prolonged Cardiac Arrest," Prehospital Emergency Care, 2010, pp. 78-84, vol. 14.
Paradis, et al., "Coronary Perfusion Pressure and the Return of Spontaneous Circulation in Human Cardiopulmonary Resuscitation," JAMA, Feb. 23, 1990, pp. 1106-1113, vol. 263.
Field, et al., "Part 1: Executive Summary: 2010 American Heart Association Guidelines for Cardiopulmonary Resuscitation and Emergency Cardiovascular Care," Circulation, 2010, pp. S640-S656, vol. 122, American Heart Association, Inc., Dallas, TX.
Shamir, et al., "Pulse oximetry plethysmographic waveform during changes in blood volume," British Journal of Anaesthesia, 1999, pp. 178-181, vol. 82(2).
Westphal, et al., "Pulse Oximetry Wave Variation as a Noninvasive Tool to Assess Volume Status in Cardiac Surgery," Clinics, 2009, pp. 337-343, vol. 64(4).
Radhakrishnan, et al., "Pulse-plethysmographic variables in hemodynamic assessment during mannitol infusion," Journal of Clinical Monitoring and Computing, 2012, pp. 99-106, vol. 26, Springer Science+Business Media, LLC.
Idris, et al., "The Relationship Between Chest Compression Rates and Outcomes from Cardiac Arrest," Circulation, Jun. 19, 2012, pp. 3004-3012, vol. 125(24), American Heart Association, Dallas, TX.
Nolan, et al., "European Resuscitation Council Guidelines for Resuscitation 2010: Section 1, Executive summary," Resuscitation, 2010, pp. 1219-1276, vol. 81, Elsevier Ireland Ltd.
Hartmann, et al., "Systematic Review and Meta-Analysis of End-Tidal Carbon Dioxide Values Associated With Return of Spontaneous Circulation During Cariopulmonary Resuscitation," Journal of Intensive Care Medicine, 2014, pp. 1-10, Sage Publications.
Lah, et al., "The dynamic pattern of end-tidal carbon dioxide during cardiopulmonary resuscitation: difference between asphyxial cardiac arrest and ventricular fibrillation/pulseless ventricular tachycardia cardiac arrest," Critical Care, 2011: http://ccforum.com/content/15/1/R13.
Reisner, et al., "Utility of the Photoplethysmogram in Circulatory Monitoring," Anesthesiology, 2008, pp. 950-958, vol. 108, American Society of Anesthesiologists, Inc. Lippincott Williams & Wilkins, Inc.
Editorial, Babbs, Charles F., "We still need a real-time hemodynamic monitor for CPR," Resuscitation, 2013, pp. 1297-1298, vol. 84, Elsevier Ireland Ltd.
Stiell, et al., "What is the role of chest compression depth during out-of-hospital cardiac arrest resuscitation?" Critical Care Medicine, 2012, pp. 1192-1198, vol. 40(4), Society of Critical Care Medicine and Lippincott Williams & Wilkins.
Letter to the Editor, Xu, et al., "Why do not we use finger pulse oximeter plethysmograph waveform to monitor the effectiveness of cardiopulmonary resuscitation?" Resuscitation, 2011, p. 959, vol. 82, Elsevier Ireland Ltd.
Cantineau, et al., "End-tidal carbon dioxide during cardiopulmonary resuscitation in humans presenting mostly with asystole: a predictor of outcome," Critical Care Medicine, May 1996, pp. 791-796, vol. 24(5), Society of Critical Care Medicine and Lippincott Williams & Wilkins.
Ornato, et al., "Relationship Between Cardiac Output and the End-Tidal Carbon Dioxide Tension," Annals of Emergency Medicine, Oct. 990, pp. 1104-1106, vol. 19(10).
Lewis, et al., "Correlation of End-Tidal CO2 to Cerebral Perfusion During CPR," Annals of Emergency Medicine, Sep. 1992, pp. 1131-1134, vol. 21(9).
Callaham, et al., "Effect of epinephrine on the ability of end-tidal carbon dioxide readings to predict initial resuscitation from cardiac arrest," Critical Care Medicine, 1992, pp. 337-343, vol. 20(3), Society of Critical Care Medicine and Lippincott Williams & Wilkins.

(56) References Cited

OTHER PUBLICATIONS

Okamoto, et al., "Changes in end-tidal carbon dioxide tension following sodium bicarbonate administration: correlation with cardiac output and haemoglobin concentration," Acta Anaesthesiologica Scandinavica, 1995, pp. 79-84, vol. 39(1).
Gruben, et al., "System for mechanical measurements during cardiopulmonary resuscitation in humans," IEEE Transactions on Biomedical Engineering, Feb. 1990, pp. 201-210, vol. 37(2).
Kern, et al., Myocardial Perfusion Pressure: A Predictor of 24-Hour Survival During Prolonged Cardiac Arrest in Dogs, Resuscitation, 1988, pp. 241-250, vol. 16, Elsevier Scientific Publishers Ireland Ltd.

\* cited by examiner

PULSE OXIMETRY-BASED CARDIO-PULMONARY RESUSCITATION (CPR) QUALITY FEEDBACK SYSTEMS AND METHODS

CROSS-REFERENCE

This application claims benefit and advantages of Chinese Patent Application No. 201310474008.7, filed Oct. 11, 2013, and Chinese Patent Application No. 201410208903.9, filed May 16, 2014, which are hereby incorporated by reference.

TECHNICAL FIELD

This disclosure relates to medical devices, and in particular relates to medical devices and their plug-ins for CPR, and CPR quality feedback methods and systems.

BACKGROUND

Cardiovascular disease has become a leading cause of global morbidity and mortality that annually results in 17 million deaths worldwide, many of which are caused by cardiac arrest. CPR is one of the most commonly used medical procedures for treating cardiac arrest. CPR may generate blood flow by directly increasing a patient's intrapleural pressure (chest compression mechanism) or by directly compressing the heart (heart pump mechanism) so that some life-sustaining blood flow can be maintained to the brain and other vital organs.

The 2010 American Heart Association Guidelines for CPR & ECC emphasized that a key to the successful resolution of a patient in cardiac arrest is to perform high-quality CPR as early as possible. High-quality CPR is defined as a compression frequency of at least about 100 times per minute and a compression depth of at least about 5 cm. Even with such high-quality CPR, however, cardiac output (CO) may reach about ¼ or ⅓ of normal CO. In clinical practice, manual or mechanical compression is often used. However, both methods are commonly associated with insufficient compression frequency and/or depth which can lead to poor CPR. Therefore, in the process of cardiac resuscitation, the CPR quality should be monitored. Although the CPR Guidelines recommend end-tidal carbon dioxide ($ETCO_2$) and invasive blood pressure monitoring for determining CPR quality, these methods require either additional specialized medical devices ($ETCO_2$) or time-consuming procedures (invasive monitoring) which make them less practical for routine clinical practice.

High-quality CPR should also involve little compression interruption. In 2013, the AHA recommended that compression time should amount to at least about 80% of an emergency treatment process. During this process, however, compression interruption may often occur due to endotracheal intubation, rescuer changeover and/or electric defibrillation. Moreover, too much compression interruption will bring about reduction in both coronary perfusion pressure and restoration rate of spontaneous circulation (and even in forward neurofunction prognosis after restoring the spontaneous circulation). Until now, there has been no monitoring means convenient for reminding the rescuer of the compression interruption situation. Although blood oxygen monitoring can show pulse oximetry waveforms caused by compression for a patient exhibiting cardiac arrest, judgment is still required as to whether there is compression interruption by manually observing the pulse oximetry waveforms, and it is impossible to measure the compression interruption time early enough for a warning.

SUMMARY OF THIS DISCLOSURE

In one aspect, a medical device includes an optical transceiver, a digital processor and an output module. The optical transceiver includes a light emitting tube and a receiving tube. The light emitting tube can emit at least one light signal to penetrate through human tissue, and the receiving tube can then receive the at least one light signal and convert the at least one light signal into at least one electrical signal. The digital processor may convert the at least one electrical signal into at least one digital signal and process the at least one digital signal to obtain peripheral circulation relevant parameters. The at least one digital signal includes at least partial hemodynamic characteristics. The output module can output associated information corresponding to the peripheral circulation relevant parameters.

In some embodiments, the peripheral circulation relevant parameters may be related to a pulsatile perfusion characteristic(s) of the human tissue. In some embodiments, during CPR, the peripheral circulation relevant parameters can include peripheral circulation parameters related to CPR quality.

In some embodiments, the peripheral circulation parameters related to CPR quality may include a first reflecting parameter that can reflect frequency variation characteristics of CPR compression, a second reflecting parameter that can reflect depth variation characteristics of CPR compression, and/or a third reflecting parameter that can reflect comprehensive variation characteristics of frequency and depth of CPR compression.

In some embodiments, the digital processor may obtain the peripheral circulation parameters related to CPR quality by identifying real-time pulsatile perfusion characteristics reflected by the at least one digital signal. The real-time pulsatile perfusion characteristic can be obtained by identifying fluctuant components and constant components in the at least one digital signal.

In some embodiments, the digital processor may obtain the first reflecting parameter by identifying a fluctuant component of the at least one digital signal and calculating frequency of the fluctuant component.

In some embodiments, the digital processor may obtain the second reflecting parameter by identifying a fluctuant component of the at least one digital signal and calculating amplitude conversion on the fluctuant component. In some other embodiments, the digital processor may obtain a corrected second reflecting parameter by identifying a fluctuant component and a constant component of the at least one digital signal and calculating an amplitude ratio of the fluctuant component and the constant component after calculating amplitude conversion on these two components.

In some embodiments, the digital processor may obtain the third reflecting parameter by identifying a fluctuant component of the at least one digital signal and calculating an area integral to the fluctuant component. In some other embodiments, the digital processor may obtain a corrected third reflecting parameter by identifying a fluctuant component and a constant component of the at least one digital signal and calculating an area ratio between an area integral to the fluctuant component and an area integral to the constant component.

In some embodiments, the digital processor can process the at least one digital signal by at least one analysis method to obtain the peripheral circulation relevant parameters reflecting CPR quality. The at least one analysis method can include a time domain analysis method and/or a frequency domain analysis method.

In some embodiments, the time domain calculation method can be based on identifying a fluctuant component and a constant component of the at least one digital signal.

In some embodiments, the time domain analysis method can calculate the peripheral circulation relevant parameters by identifying frequency characteristic, amplitude characteristic and/or area characteristic of the at least one digital signal, and the frequency domain analysis method can be used for frequency spectrum identification based on a non-zero frequency spectrum or used for frequency spectrum identification based on a ratio between a non-zero frequency spectrum and a zero-frequency spectrum.

In some embodiments, the time domain analysis method may identify the amplitude characteristic and the area characteristic of the at least one digital signal based on the fluctuant component of the at least one digital signal or based on a ratio between the fluctuant component and the constant component of the at least one digital signal.

In some embodiments, the associated information can include one or more of the following information: video information, audio information and light information which correspond to the peripheral circulation relevant parameters.

In some embodiments, the output module can be a display module to display the video information. The video information may include a tendency chart which can reflect dynamic variations of the peripheral circulation relevant parameters. The video information on the tendency chart may include target range information on the peripheral circulation relevant parameters which are related to standard CPR quality; a first warning when the peripheral circulation relevant parameters exceed their target range; and a second warning when the dynamic variations of the peripheral circulation relevant parameters exceed their optimal variation range.

In some embodiments, the audio information may refer to auditory sense based on sound variation, and the light information may refer to visual sense based on light frequency.

In another aspect, a medical device plug-in can include an enclosure component, a signal acquisition interface, a signal processing module and an interactive interface. The signal acquisition interface can be positioned on an external surface of the enclosure component and connected with signal acquisition accessories. The signal processing module positioned in the enclosure component can obtain acquisition signals through the signal acquisition interface, convert the acquisition signals into digital signals, and obtain peripheral circulation relevant parameters through calculation based on the digital signals. The interactive interface can recognize the information interaction between a host and the signal processing module. The digital signals include at least partial peripheral circulation characteristics.

In some embodiments, the enclosure component may protect the signal processing module from being damaged by external interferences. The external interferences can include impact of light, and electromagnetic and external forces.

In some embodiments, the signal processing module can comprise a signal sampling circuit, a digital processor and a data communication circuit. The signal sampling circuit can obtain the electrical signals from the signal acquisition interface and convert the electrical signals into digital signals. The digital processor can then calculate the peripheral circulation relevant parameters based on the digital signals.

In some embodiments, an operating mode of the interactive interface and the signal processing module can be at least partially controlled by the host. The signal processing module may automatically adjust its operating mode according to host settings. The signal processing module may automatically transmit the peripheral circulation relevant parameters obtained through calculation to the host according to host settings.

In some embodiments, operation of the interactive interface and the signal processing module can rely on energy supply from the host.

In some embodiments, during CPR, the peripheral circulation relevant parameters can include peripheral circulation parameters related to CPR quality, which can include a first reflecting parameter to reflect frequency variation characteristics of CPR compression, a second reflecting parameter to reflect depth variation characteristics of CPR compression, and a third reflecting parameter to reflect comprehensive variation characteristics of frequency and depth of CPR compression.

In some embodiments, the CPR quality can be reflected through fluctuation characteristics and the stability level of the peripheral circulation relevant parameters as well as conformity of the peripheral circulation relevant parameters with their target range.

In still another aspect, a CPR quality feedback method may include processing one or more of at least two measured signals to calculate peripheral circulation relevant parameters. This method may further include confirming pulsatile perfusion signals according to the measured signals, calculating the peripheral circulation relevant parameters according to the pulsatile perfusion signals and displaying the peripheral circulation relevant parameters on a display interface.

In yet another aspect, a CPR quality feedback method may process one or more of at least two measured signals to calculate peripheral circulation parameters related to CPR quality based on the measured signals. The peripheral circulation parameters related to CPR quality can include one or more of the following parameters: a first reflecting parameter, a second reflecting parameter and a third reflecting parameter. The first reflecting parameter may reflect frequency variation characteristics of CPR compression, the second reflecting parameter may reflect a depth variation characteristics of CPR compression, and the third reflecting parameter may reflect comprehensive variation characteristics of frequency and depth of CPR compression.

In still another aspect, a medical device can include a blood oxygen probe, a blood oxygen module and an output module. The blood oxygen probe can probe measured positions of a test subject and detect blood oxygen signals of the test subject in real time. The blood oxygen module can acquire the blood oxygen signals outputted from the blood oxygen probe, generate a pulse oximetry waveform based on the blood oxygen signals, calculate peripheral circulation parameters related to CPR quality based on the pulse oximetry waveform, and output associated information on the peripheral circulation parameters related to CPR quality. The output module can provide feedback on the associated information outputted by the blood oxygen module on the peripheral circulation parameters related to CPR quality.

In some embodiments, the peripheral circulation parameters related to CPR quality may include blood oxygen frequency characteristics of the pulse oximetry waveform and peripheral circulation parameters generated by compression. The peripheral circulation parameters generated by compression may include amplitude characteristics of a single pulse wave and/or area characteristics of a single pulse wave.

In some embodiments, the blood oxygen module can separate a constant component and a fluctuant component from the pulse oximetry waveform and calculate the blood oxygen frequency characteristic and the peripheral circulation parameters generated by compression based on the fluctuant component of the pulse oximetry waveform or a ratio between the fluctuant component and the constant component of the pulse oximetry waveform.

In some embodiments, the output module can be a display module to display a waveform graph of the amplitude characteristic and/or the area characteristic on a display interface. The display module can further display an amplitude distribution range limit and/or an area distribution range limit related to a standard value of chest compression quality on the waveform graph of the amplitude characteristic and/or the area characteristic.

In some embodiments, the blood oxygen module can calculate a fluctuating value of the amplitude characteristic, evaluate whether the fluctuating value of the amplitude characteristic is less than a first preset value and whether the amplitude characteristic falls within an amplitude distribution range limit, and, if so, the blood oxygen module may output a first prompt message to inform a user that current compression quality has reached the standard, threshold, or selected limit.

In some embodiments, the blood oxygen module can calculate a fluctuating value of the area characteristic, evaluate whether the fluctuating value of the area characteristic is less than a second preset value and whether the area characteristic is within an area distribution range limit, and, if so, the blood oxygen module may output a second prompting message to inform a user that current compression quality has reached the standard.

In some embodiments, the amplitude characteristic can include an absolute amplitude value or an amplitude index, and the area characteristic can include an absolute area value or an area index. The amplitude index can be a ratio between the absolute amplitude value of a single pulse wave of the fluctuant component of an amplified pulse oximetry waveform and corresponding DC value of the amplified pulse oximetry waveform. The area index can be a ratio between the absolute area value of a single pulse wave of the fluctuant component of an amplified pulse oximetry waveform and corresponding DC component of the amplified pulse oximetry waveform.

In some embodiments, the medical device may further comprise an interaction control interface which may be connected with another medical device to recognize data communication between these two medical devices. The blood oxygen module can adjust configuration and output of another medical device through the interaction control interface. The configuration and output may include one or more of compression depth, compression frequency and compression time phase.

In some embodiments, that another medical device or equipment can be a CPR instrument.

In some embodiments, the medical equipment can also include a control module. The control module can have a signal connection with the interaction control interface and the blood oxygen module, and may at least operate to control the compression frequency and the compression depth of that another medical equipment. The blood oxygen module may also calculate a fluctuating value of the amplitude characteristic, evaluate whether the fluctuating value of the amplitude characteristic is less than a first preset value and whether the amplitude characteristic falls within an amplitude distribution range limit. If the fluctuating value of the amplitude characteristic is less than the first preset value but the amplitude characteristic does not fall within the amplitude distribution range limit, the blood oxygen module may output a first result information to the control module, and the control module can notify that another medical equipment to increase the compression depth according to the first result information.

In some embodiments, the control module can have a signal connection with the interaction control interface, the blood oxygen module and the output module, and can at least operate to control the compression frequency and the compression depth of that another medical equipment. The blood oxygen module can also calculate a fluctuating value of the area characteristic, evaluate whether the fluctuating value of the area characteristic is less than a second preset value and whether the area characteristic falls within an area distribution range limit. If the fluctuating value of the area characteristic is less than the second preset value but the area characteristic does not fall within the area distribution range limit, the blood oxygen module may output a second result information to the control module, and the control module can notify that another medical equipment to increase the compression depth according to the second result information. If the area characteristic falls within the area distribution range limit and the fluctuating value of the area characteristic is less than the second preset value, the blood oxygen module may output a third result information to the control module, and the control module can notify that another medical equipment to increase the compression depth according to the third result information and provide feedback on increasing the compression depth to the blood oxygen module. Based on this feedback, the blood oxygen module can calculate the area characteristic of single pulse wave after increasing the compression depth and evaluate whether the area characteristics of a single pulse wave after increasing the compression depth is at a maximum value. If not, the blood oxygen module may output a fourth result information; if so, the blood oxygen module may output a fifth result information. The control module can notify that another medical equipment to increase the compression depth according to the fourth result information, or control that another medical equipment to maintain the current compression depth according to the fifth result information. In some other embodiments, the blood oxygen module may also output a third prompt message when the area characteristic of a single pulse wave after increasing the compression depth is at the maximum value. The third prompt message can inform the user that the test subject has reached an optimal compression state of stroke volume.

In some embodiments, the blood oxygen module is capable of obtaining a pulse waveform comprising one or more single pulse waves based on fluctuant components that are separated from the pulse oximetry waveform, and then counting a disappearing period of the pulse wave by evaluating a characteristic variation of one or more pulse waves.

In some embodiments, the blood oxygen module can count the duration of the disappearing period of the pulse wave and/or calculate a total time percentage of the disappearing period of the pulse wave.

In some embodiments, the blood oxygen module is also capable of counting a compression period in which the pulse wave is generated. The blood oxygen module can count duration of the disappearing period of the pulse wave and/or a total time percentage of the disappearing period of the pulse wave, and count duration of the compression period and/or a total time percentage of the compression period.

In some embodiments, the blood oxygen module may preset a first threshold, a second threshold and a third threshold, and prompt a warning when the duration of the disappearing period of the pulse wave is larger than the first threshold, when the total time percentage of the disappearing period of the pulse wave is larger than the second threshold, and/or when the total time percentage of the compression period is smaller than the third threshold.

In some embodiments, during CPR, peripheral circulation relevant parameters can include peripheral circulation parameters related to CPR quality, where the peripheral circulation parameters related to CPR quality may include a first reflecting parameter, a second reflecting parameter and a third reflecting parameter, which may reflect, respectively, frequency variation characteristics, depth variation characteristic and comprehensive variation characteristic of frequency and depth of CPR compression. In some embodiments of this disclosure, the peripheral circulation parameters related to CPR quality may further refer to those parameters obtained based on pulse oxymetry.

In an embodiment, peripheral circulation parameters related to CPR quality can include the frequency characteristic of pulse oximetry waveforms and peripheral circulation parameters generated by compression, where the peripheral circulation parameters generated by compression may include amplitude characteristic of a single pulse wave and/or area characteristics of a single pulse wave.

In some embodiments, the first reflecting parameter can be determined by frequency identification on measured signals containing at least partial hemodynamic characteristics (for example, pulse oximetry waveforms); the second reflecting parameter can be determined by amplitude conversion on the measured signals containing the at least partial hemodynamic characteristics; and the third reflecting parameter can be determined by area integration of the measured signals containing the at least partial hemodynamic characteristics.

Embodiments of this disclosure can calculate the peripheral circulation relevant parameters based on the measured signals containing the at least partial hemodynamic characteristics. By using these parameters, timely feedback on CPR quality can be obtained, including the compression depth and the compression frequency. Since the signals are measured in vitro, it is non-invasive to the patient, so that real-time feedback on CPR quality can be obtained in a non-invasive manner. In addition, when the pulse oximetry waveform is used as the basis for calculating the peripheral circulation parameters, raw data of oxygen saturation of blood can be calculated, so that additional feedback devices may not be needed.

In some embodiments, a pulse oximeter plug-in used for CPR quality feedback can be manufactured as an independent pluggable module that may be used together with bedside equipment.

DETAILED DESCRIPTION

Figure 1:
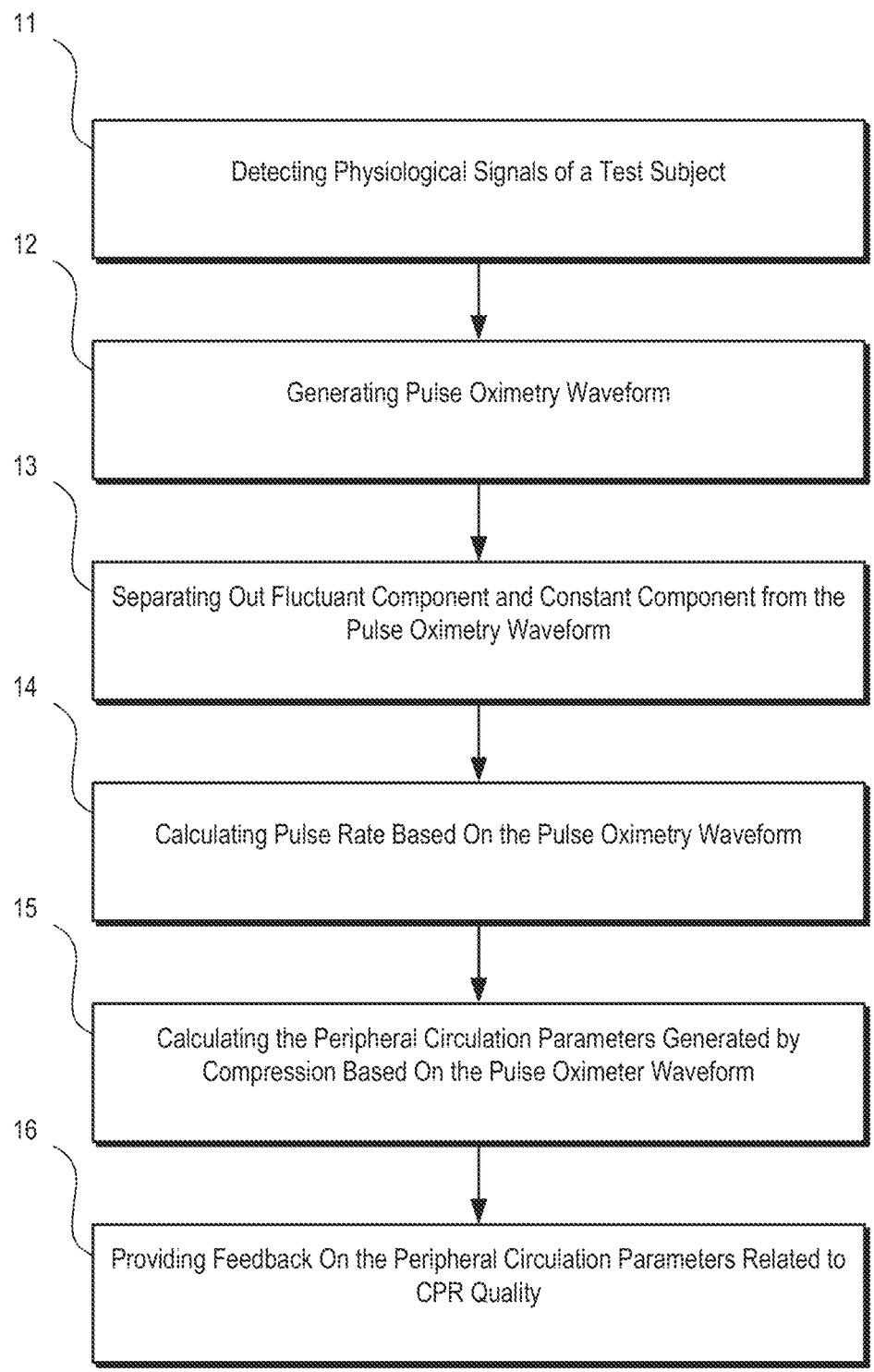
FIG. 1 is a flow chart of CPR quality feedback according to an embodiment of this disclosure.

This disclosure is further described in detail with reference to specific implementations and accompanying drawings.

This disclosure provides medical devices, methods and medical device plug-ins for CPR quality feedback (control) based on signals containing at least partial hemodynamic characteristics. The signals containing the at least partial hemodynamic characteristics can be obtained by acquiring and converting variation signals of absorbed light that can penetrate through human tissue such as commonly obtained through pulse oximetry. Real-time pulsatile perfusion characteristics of signals can be identified by separating their constant component and their fluctuant component. In addition, based on these separated fluctuant components or a ratio between the fluctuant component and the constant component, peripheral circulation relevant parameters can be obtained to extrapolate CPR quality.

Determination of oxygen saturation may include two parts, namely spectrophotometric determination and blood plethysmography. The spectrophotometric determination can be performed by using red light with a wavelength of about 660 nm and infrared light with a wavelength of about 940 nm. Oxyhemoglobin ($HbO_2$) has less absorption for 660 nm red light and more absorption for 940 nm infrared light, while deoxygenated hemoglobin (Hb) has more absorption for 660 nm red light and less absorption for 940 nm infrared light. When determining oxygen saturation, some biological tissues may first be illuminated respectively by red light and infrared light, and the red light and the infrared light that penetrate through the biological tissue can then be detected on an opposite side of the biological tissues through a photoelectric detector. Corresponding electrical signals may be outputted from the photoelectric detector and a ratio between the infrared light absorption intensity and the red light absorption intensity can be calculated so as to determine an oxygenation degree of hemoglobin, namely oxygen saturation ($SaO_2$).

When determining blood oxygen saturation, blood perfusion should be provided. When a light beam transilluminates a peripheral tissue, the attenuation degree of transilluminated light energy detected may be related to cardiac cycle. At the time of systole, peripheral blood volume is maximal, and light absorption intensity reaches a maximum value and causes the detected light energy to reach its minimum value. The opposite is true at diastole. Variations of light absorption intensity reflect variations of blood volume. Varying the blood volume can change the intensity of transilluminated light energy. Absorption at each wavelength can be a function of skin color, skin structure, iliacus muscle, blood and other tissues penetrated by the light. The light absorption intensity can be considered as a sum of pulsate absorption and non-pulsate absorption. The AC component can be caused by pulsatory arterial blood, while the DC component may be constant absorption caused by the light absorption intensities of non-pulsatory arterial blood, venous blood and tissues. Perfusion index PI is a percentage of AC in DC (PI=AC/DC×100%). The AC component and the DC component are respectively described as the fluctuant component and the constant component hereinafter.

The pulse oximetry waveform, referring to a series of data obtained by real-time acquisition of electrical signals of the red light or the infrared light that penetrates through the biological tissues, can be used to calculate oxygen saturation. In some cases, such data may include sampling value and time information. Based on the detected red light and infrared light transmission signals, the pulse oximetry waveform of red light and the pulse oximetry waveform of infrared light can be obtained. Oxygen saturation waveform based on these two pulse oximetry waveforms can also be calculated. The pulse oximetry waveform may have certain relevancy to CPR quality.

The amplitude and area under the curve (AUC) of the pulse oximetry waveform may have relevancy to hemodynamic indexes of test subjects including cardiac output (CO) and peripheral tissue perfusion. It is also discovered that the pulse oximeter amplitude and area under the curve (AUC) can reflect a peripheral circulation state, and the frequency of the oximetry waveform can reflect the frequency of chest compression. In the process of CPR, the peripheral circulation state may depend on a quality of artificial circulation, while the quality of artificial circulation may depend on the depth and frequency of chest compression.

An embodiment of this disclosure describes a CPR quality feedback method, which can calculate peripheral circulation parameters related to CPR quality based on a pulse oximetry waveform and use the calculated peripheral circulation parameters related to CPR quality to provide feedback on CPR quality. The peripheral circulation parameters related to CPR quality can include parameters that may be used to provide feedback on the compression frequency and the compression depth in the CPR process. In this embodiment, the blood oxygen frequency characteristic of the pulse oximetry waveform can be used to provide feedback on the compression frequency in the CPR process, while the amplitude characteristic and/or area characteristic of the pulse oximetry waveform can be used to provide feedback on the compression depth in the CPR process.

Two data processing methods, namely time domain analysis and frequency domain analysis, will be described in detail. In an example of this embodiment, the time domain analysis method can be used for digital signal data processing. The flow of the CPR quality feedback is shown in FIG. 1 and may include the following steps (steps 11-16).

Figure 2:
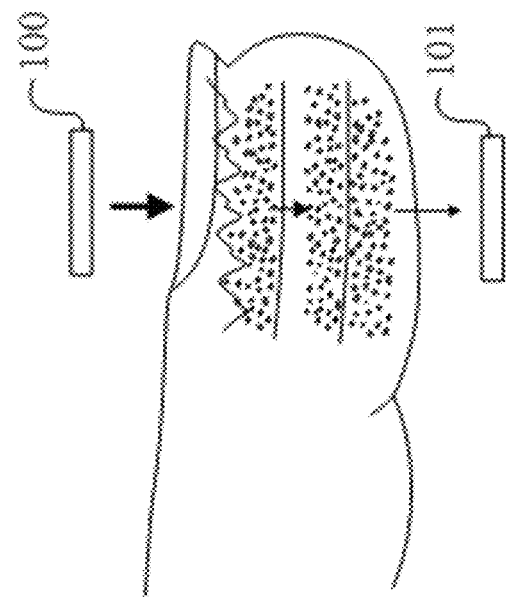
FIG. 2 is a schematic diagram for blood oxygen detection according to an embodiment of this disclosure.

Physiological signals (in this case, blood oxygen signals) are detected in step 11. When performing CPR on a test subject, a blood oxygen probe can be employed to detect a measured position of the test subject undergoing CPR and to detect the blood oxygen signal of the test subject in real time. In the embodiment of this disclosure, since the process of providing feedback on the CPR quality may involve the blood oxygen frequency characteristic, the amplitude characteristic and the area characteristic of the pulse oximetry waveform, the ratio between red light and infrared light transmission signals may not be needed. Therefore, either of the pulse oximetry waveforms of red light and infrared light can be used. For the convenience of illustration, any of those two pulse oximetry waveforms is referred to as pulse oximetry waveform. As shown in FIG. 2 illustrating an embodiment, a light-emitting device 100 is installed on one side of the blood oxygen probe while a photoelectric detector 101 is installed on the other side. The light-emitting device 100 can be a red light or an infrared light emitting tube, or it may also include the two emitting tubes (red light and infrared light emitting tubes). The photoelectric detector 101 may convert the detected red light or infrared light that penetrates through the arterial blood vessel of the finger into electrical signals.

In step 12, the pulse oximetry waveform can be generated based on the acquired blood oxygen signals. Skin, muscle, fat, venous blood, pigment and bone have a constant absorption coefficient for red light or infrared light, while $HbO_2$ and Hb concentrations in arterial blood flow have periodic variations with the arterial pulsation of blood, leading to periodic variations in the intensity of the signals outputted by the photoelectric detector 101. The original pulse oximetry waveform can be obtained by processing (e.g., by signal amplification and/or filtering) these electrical signals having periodic variations.

Figure 3:
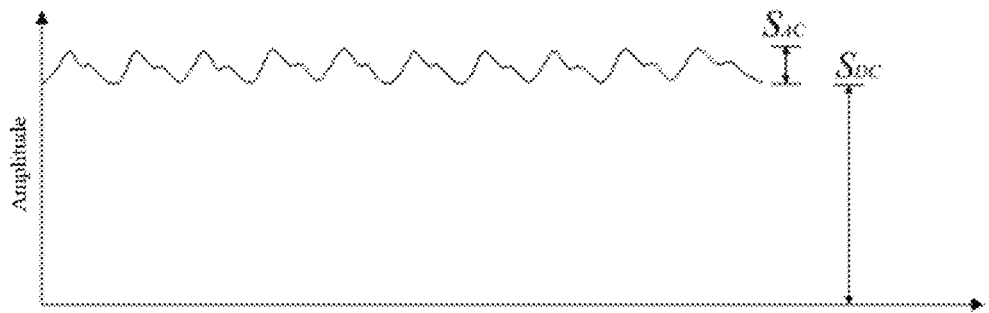
FIG. 3 shows a waveform of original blood oxygen signals.

In step 13, the constant component and fluctuant component can be separated from the pulse oximetry waveform. As shown in FIG. 3, the original signals may include the fluctuant component $S_{AC}$ and the constant component $S_{DC}$.

Figure 4:
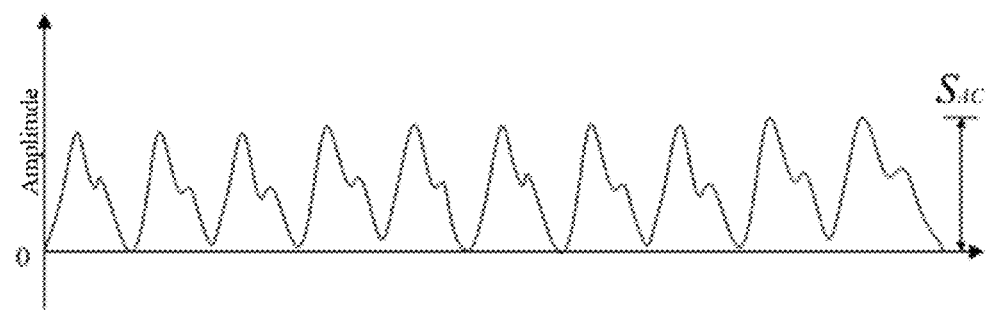
FIG. 4 shows a waveform of a fluctuant component separated from original blood oxygen signals.

In some cases, factors such as body movement and background light interference may result in a drift of the constant component $S_{DC}$ over time, i.e., its numerical value may not be constant but can fluctuate with time. The AC component may be related to pulsating blood volume. When blood flow is weakest, the blood light absorption intensity is at minimum, the transmission signal is strongest, and the AC signal reaches a maximum value. When blood flow is strongest, its light absorption intensity is at maximum, the transmission signal is weakest, and the AC signal reaches its minimal value. The DC component may be related to the light transmission through non-pulsating tissues such as muscle and bone, and the constant component can be the minimum value of the signal. By using suitable technologies such as value averaging, smooth filtering technology, FIR/IIR filtering technology or curve fitting technology, the constant component $S_{DC}$ can be filtered out of the original signals and the fluctuant component $S_{AC}$ can be left for further data processing. The waveform of the separated fluctuant component is shown in FIG. 4.

In step 14, the blood oxygen frequency characteristic of the pulse oximetry waveform can be calculated based on its fluctuant component. The fluctuant component $S_{AC}$ may be related to the blood flow, and its frequency can be consistent with CPR compression frequency. The formula is as follows:

$$F_{CPR} = f_{S_{AC}} \quad (1)$$

Where $F_{CPR}$ represents the CPR compression frequency, $f_{S_{AC}}$ represents the frequency of the fluctuant component $S_{AC}$, and the unit of both is Hertz (Hz).

The frequency of the fluctuant component $S_{AC}$ can be multiplied by 60, so as to obtain the blood oxygen frequency characteristic, namely CPR compression degree/min (i.e., times per minute). Its formula is as follows:

$$\mathrm{Deg}_{CPR} = F_{CPR} * 60 = f_{S_{AC}} * 60 \quad (2)$$

Where $\mathrm{Deg}_{CPR}$ represents the CPR compression degree/min.

In this step, the blood oxygen frequency characteristic of the pulse oximetry waveform may be calculated based on the fluctuant component. In another example, the blood oxygen frequency characteristic can also be calculated based on the original pulse oximetry waveform. Therefore, this step may be exchanged with step 13.

In step 15, the peripheral circulation parameters generated by compression can be calculated based on the fluctuant component of the pulse oximetry waveform. In an example, the peripheral circulation parameters generated by compression may include the amplitude characteristic of a single pulse wave. Since the pulse oximetry waveform can have periodic fluctuations, the range from a wave hollow to an adjacent wave crest is defined as a single pulse wave in an embodiment of this disclosure. In this step, the absolute amplitude value of the single pulse wave can be calculated in response to the single pulse wave signal of the fluctuant component $S_{AC}$ and then used to evaluate the variations in compression depth during CPR. The amplitude value can be calculated by using any suitable techniques such as maximum amplitude selection method (max amplitude), average amplitude selection method (average amplitude) or root mean square method, thereby extracting the absolute amplitude value of each single pulse wave in the fluctuant component. In this embodiment, the root mean square method may be used to extract the absolute amplitude value $\mathrm{Amp}_{CPR}$ of each single pulse wave in the fluctuant component. The formula is as follows:

$$\mathrm{Amp}_{CPR} = \sqrt{\frac{\sum_{n=0}^{N-1} S_{AC}^2(n)}{N}} \quad (3)$$

Where $S_{AC}(n)$ represents the $n^{th}$ sampling data point of a single pulse wave, and N represents the total data length of a single pulse wave, namely the total sampling point count of a single pulse wave. $\mathrm{Amp}_{CPR}$ represents the absolute amplitude value of a single pulse wave, which can reflect the depth change in the CPR compression process. In general, the sampled data is in voltage. Therefore, the unit of such absolute amplitude value $\mathrm{Amp}_{CPR}$ can be defined as PVA (Pulse Oximeter Voltage Amplitude).

In another example, the peripheral circulation parameters generated by compression, which are related to the hemodynamic effect, may also include the area characteristic of a single pulse wave. In this step, the absolute area value of a single pulse wave can be calculated according to the single pulse wave signal of the fluctuant component $S_{AC}$ and used to evaluate the variations of stroke volume in the CPR process. The absolute area value of the single pulse wave can be calculated by any suitable techniques such as area integral method, which may be applicable to both continuous and discrete signals. In this embodiment, based on the features of a fixed sampling frequency of blood pulse oximetry, the method of point-by-point accumulation integral can be used to calculate the absolute area parameter. The formula is as follows:

$$\mathrm{Area}_{CPR} = \sum_{n=0}^{N-1} S_{AC}(n) \quad (4)$$

Where $S_{AC}(n)$ represents the $n^{th}$ sampling data point of a single pulse wave, and N represents the total data length of a single pulse wave, namely the total sampling point count of a single pulse wave. $\mathrm{Area}_{CPR}$ represents the absolute area value of a single pulse wave, which can indirectly reflect the variation of the stroke volume in the CPR compression process. In general, the sampled data is a voltage value. Therefore, the unit of such absolute area value $\mathrm{Area}_{CPR}$ can be defined as: PVPG (Pulse Oximeter Voltage Plethysmography), which is also called voltage volume.

Those skilled in the art should understand that the peripheral circulation parameters related to CPR quality may also include not only amplitude characteristics but also area characteristics, both of which may be calculated in this step.

The feedback on the peripheral circulation parameters related to CPR quality, which are based on a pulse oximeter, is provided in step 16. The feedback mode can be video and/or audio prompt. For example, the values of the calculated parameters may be displayed directly. Those parameters can also be first compared with an evaluation standard, the result of whether such parameters comply with the standard may be obtained, and then the result can be displayed.

Figure 5:
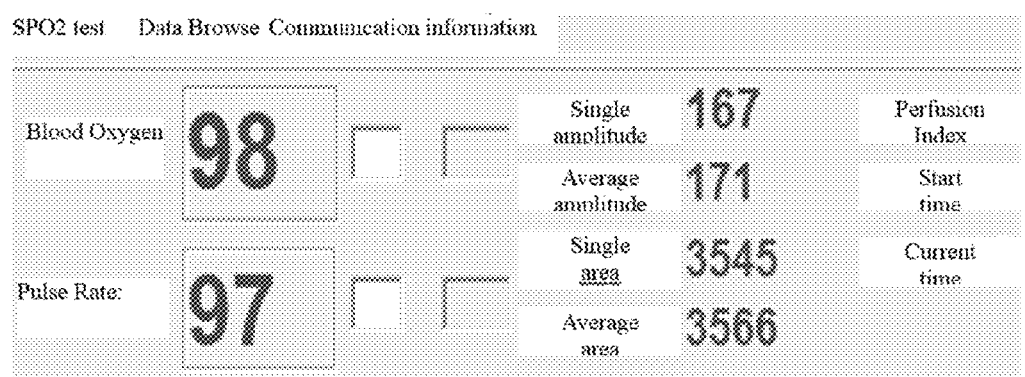
FIG. 5 is a schematic diagram of providing feedback on peripheral circulation parameters related to a pulse oximeter in text display mode according to an embodiment of this disclosure.

The feedback mode may also include text display. As shown in FIG. 5, the blood oxygen frequency characteristic, the single amplitude and the single area are displayed.

For the blood oxygen frequency characteristic, the guideline requests that, when the compression frequency is at least about 100 times per minute, it may be concluded that the compression frequency quality meets the standard or determined limit (this index can be modified as more clinical application data becomes available). In a clinical CPR application process, medical personnel can evaluate whether the CPR compression frequency meets the standard or determined limit or is stable by observing the stability of the blood oxygen frequency characteristic value and/or the pulse rate parameter on a display interface. Under the precondition of complying with the specifications of the guideline, the medical personnel may adjust the CPR compression frequency, so that the blood oxygen frequency characteristic can provide feedback and control the CPR compression frequency.

The amplitude characteristic can be used to provide feedback on the compression depth. In general clinical practice, according to the specifications of the guideline, when the compression depth reaches at least about 5 cm, it may be deemed that the compression depth basically meets the standard or determined limit (this index can be modified according to a large amount of clinical application data). Theoretically, $Amp_{CPR}$ should exhibit linear correlation with the compression depth. When the compression depth is stable, the parameter values of $Amp_{CPR}$ should be stable with less fluctuation. In a clinical CPR application process, the compression may be unstable at the beginning stage, and thus the index values of $Amp_{CPR}$ can be unstable with significant fluctuations. With the stabilization of compression depth, the index values of $Amp_{CPR}$ can become relatively stable, i.e., those values can be maintained within a small range of fluctuations. In such case, it may be concluded that the CPR compression depth has met the standard or determined limit.

The area characteristic can be used to indirectly reflect the stroke volume. Theoretically, $Area_{CPR}$ should exhibit a linear positive correlation with cardiac ejection volume in every compression. When the compression depth is stable and the compression frequency is constant, the parameter value of $Area_{CPR}$ should be stable with less fluctuation. In a clinical CPR application process, the compression depth and the compression frequency may be unstable at the beginning stage, and thus the outputted index values of $Area_{CPR}$ may also have large fluctuations, i.e., a large variable range of index values. When the compression depth and the compression frequency become stable, the index values of $Area_{CPR}$ should also exhibit relatively stable characteristics, i.e., the variations in index values should fall within a relatively small range of fluctuations. In this case, it may be concluded that the CPR effect is stable.

In addition, the stroke volume may indicate a maximum output limit for different patients. When the compression has reached a certain extent, if the stroke volume cannot be improved by increasing the depth and frequency, it may be concluded that the maximum cardiac output under compression has been achieved on this patient. According to this characteristic, when $Area_{CPR}$ is at a relatively stable state, the tester may make adjustment(s) of depth and frequency and then observe the variations in the parameter values of $Area_{CPR}$. If the parameter values of $Area_{CPR}$ have reached a maximum value (for example, if it fluctuates within down to about 10% or 5%, or if it no longer increases with an increase of compression depth), it may be concluded that an optimal compression state of stroke volume has been found. The evaluation standard for the maximum value is a parameter, which can be adjusted according to actual clinical effect.

When the cardio-pulmonary function of the human body has stopped, the respective physiologic differences of the human body may also decrease accordingly. At this time, it may be considered that the human body environment is substantially consistent, while CPR manual intervention has a relatively stable compression depth and compression frequency. This can provide a basis for establishing the CPR measurement indexes. CPR compression depth and compression frequency can cause variations in cardiac output. The compression depth may affect the stroke volume, while the variations in stroke volume can be indirectly reflected as the single area variations of the blood oxygen pulse wave and the amplitude variations of a single blood oxygen pulse wave; the fixed absorption of retained blood, finger bone and finger tissue may be indirectly embodied as the DC components of the single pulse signals of the blood oxygen pulse wave. Therefore, the amplitude characteristic and/or the area characteristic of a single pulse wave can be used to provide feedback on the CPR quality.

In such embodiment, the absolute amplitude value of $Amp_{CPR}$ and/or the absolute area value of $Area_{CPR}$ can be used to measure the CPR implementation effect based on the absolute value of the signal. According to the trend variation and the stability of the parameter values of both $Amp_{CPR}$ and $Area_{CPR}$, whether the CPR implementation has reached an optimal state can be evaluated. However, the absolute amplitude value of $Amp_{CPR}$ and the absolute area value of $Area_{CPR}$ may be affected by the variations in the drive current of a blood oxygen module and thus may not be used for other people in a quantitative manner (i.e., people may have inconsistent parameter values). In addition, according to the characteristics of the blood oxygen system, in order for the sampled blood oxygen signals to fall within a measurable range, the signal conditions (such as by regulating the drive current) may have to be amplified or reduced, and the pulse oximetry waveform can then be generated according to the amplified/reduced blood oxygen signals. The variations in the drive current may result in the variations in the fluctuant component and the constant component of the signals to the same degree.

Figure 6:
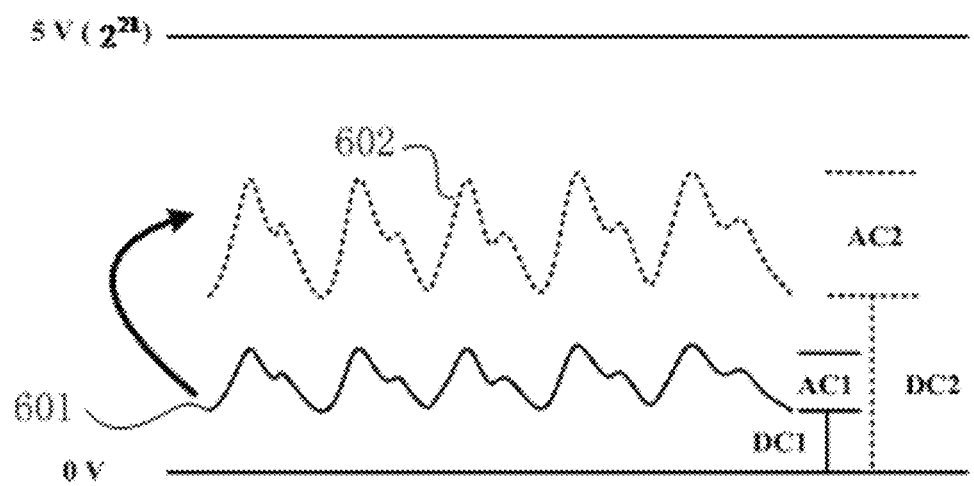
FIG. 6 shows a waveform of amplified blood oxygen signals according to an embodiment of this disclosure.
Figure 7:
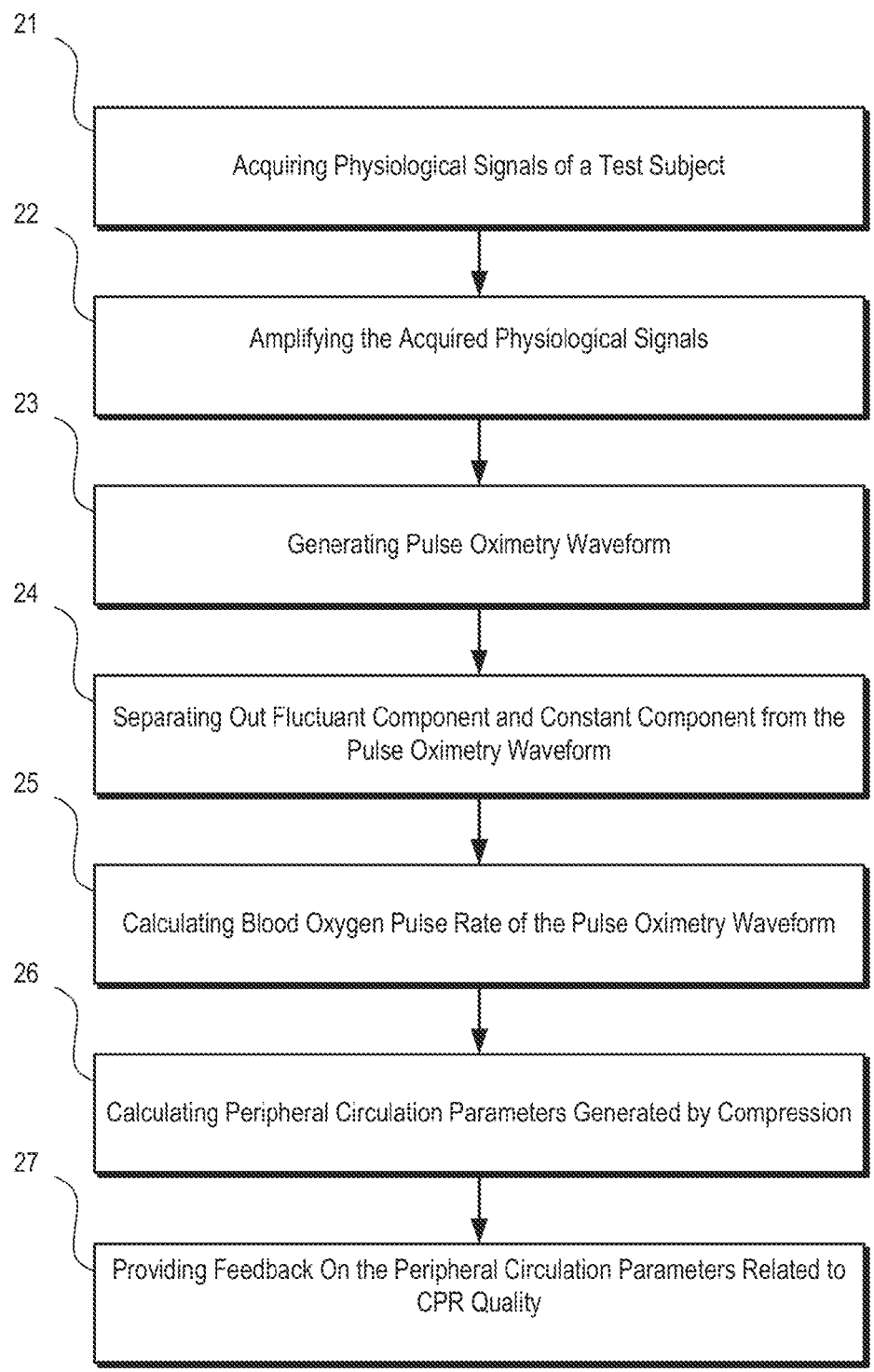
FIG. 7 is a flow chart of CPR quality feedback according to another embodiment of this disclosure.

In this embodiment, the blood oxygen signals can be amplified. As shown in FIG. 6, the measurement range is about 0-5V, and the signal in solid line 601 falls within a lower measuring range. In this case, drive regulation can be made so that the signals would fall within a reasonable measurement range. For example, after a double drive regulation, the signal in dotted line 602 as shown in the figure is located at a middle position of the measurement range, the original fluctuant component AC1 is adjusted to AC2, and the original constant component DC1 is adjusted to DC2. According to the drive characteristic, it is known that: AC2=AC1*2 and DC2=DC1*2. In such case, the flow of the CPR quality feedback method in this embodiment is shown in FIG. 7, which can include the following steps 21-27.

The blood oxygen signals of the test subject can be detected in step 21. The detection mode is the same as that of step 11.

The acquired blood oxygen signals may be amplified in step 22.

The pulse oximetry waveform can be generated based on the amplified blood oxygen signals in step 23.

The constant and fluctuant components may be separated from the pulse oximetry waveform in step 24.

The blood oxygen frequency characteristic of the pulse oximetry waveform can be calculated based on the pulse oximetry waveform or its fluctuant component in step 25. The calculation mode is the same as that in step 14.

In step 26, the peripheral circulation parameters generated by compression can be calculated based on the fluctuant components of the pulse oximetry waveform. The peripheral circulation parameters generated by compression may include the amplitude characteristic and/or the area characteristic of a single pulse wave. In this step, in addition to the absolute amplitude value and/or the absolute area value of a single pulse wave, an amplitude index of a single pulse wave and/or an area index of a single pulse wave may also be calculated.

The amplitude index of a single pulse wave refers to a ratio between the absolute amplitude value of a single pulse wave and the corresponding DC component, and its calculation formula is as follows:

$$AmpIndex_{CPR} = \frac{\sqrt{\frac{\sum_{n=0}^{N-1} S_{AC}^2(n)}{N}}}{\left(\sum_{n=0}^{N-1} S_{DC}(n)\right)/N} \quad (5)$$

where $S_{DC}(n)$ refers to the $n^{th}$ sampling data point of the DC component, N refers to the sampling number, and $AmpIndex_{CPR}$ refers to the amplitude index of a single pulse wave. In general, the sampled data is measured in voltage. Therefore, the unit of the amplitude index $AmpIndex_{CPR}$ can be defined as PVAI (Pulse Oximeter Voltage Amplitude Index).

$AmpIndex_{CPR}$ is a quantization parameter which may eliminate the influence of the drive regulating factor on the amplitude, reflecting the variation characteristic of the compression depth, resulting in the removal of interfering drive regulation input.

The area index of the single pulse wave refers to a ratio between the absolute area value of the single pulse wave and the corresponding DC component, and its calculation formula is as follows:

$$AreaIndex_{CPR} = \frac{Area_{CPR}}{\left(\sum_{n=0}^{N-1} S_{DC}(n)\right)/N} = \frac{\sum_{n=0}^{N-1} S_{AC}(n)}{\left(\sum_{n=0}^{N-1} S_{DC}(n)\right)/N} \quad (6)$$

where $AreaIndex_{CPR}$ refers to the area index of a single pulse wave. In general, the sampled data is in volts. Therefore, the unit of the area index $AreaIndex_{CPR}$ can be defined as PVPI (Pulse Oximeter Voltage Plethysmography Index), also called the voltage volume index.

The area index $AreaIndex_{CPR}$ may reduce the individual difference, remove the interference from drive regulation and thus have sound anti-interference capacity.

In step 27, the feedback on peripheral circulation parameters related to CPR quality, which are based on a pulse oximeter, are provided.

Feedback on the peripheral circulation parameters related to CPR quality can be provided in other embodiments, or can be provided as described below.

The amplitude characteristic can be related to the compression depth, while the area characteristic can be related to the compression depth and the compression frequency. The guideline has certain specifications on the compression depth and the compression frequency. When such specifications are met, it can be concluded that the CPR quality has reached the standard or determined limit. If the tester can find the mapping values of the amplitude characteristic and the area characteristic which correspond to the basic standard values specified in the guideline, the amplitude characteristic and the area characteristic can be directly compared with their mapping values so as to evaluate whether the CPR quality basically meets the standard or determined limit. These mapping values constitute distribution range limits of the amplitude or area characteristics.

Figure 8A:
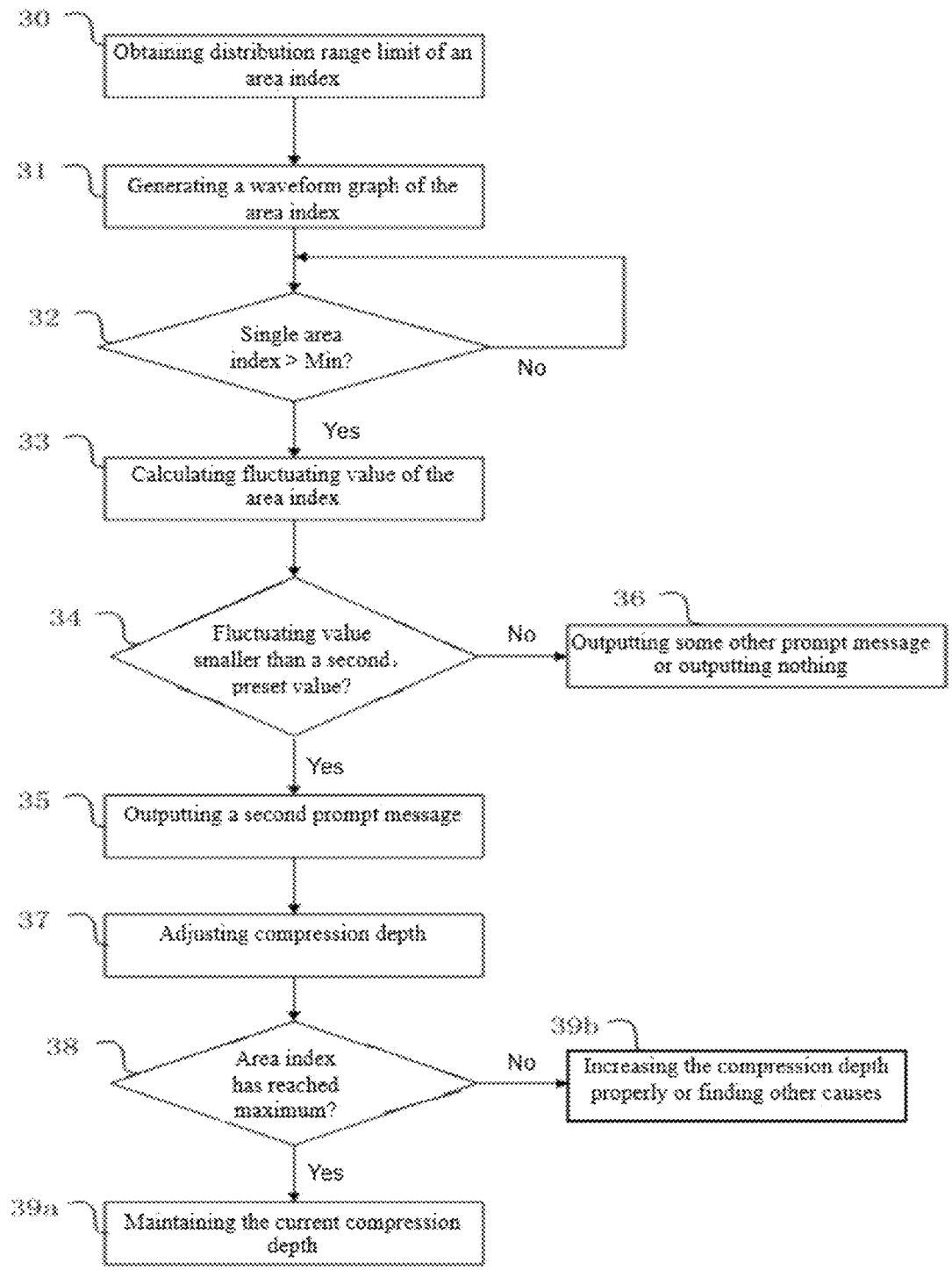
FIG. 8a is a flow chart of providing pulse oximeter-based feedback on peripheral circulation parameters according to an embodiment of this disclosure.

Using the area index $AreaIndex_{CPR}$ in the area characteristic as an example, feedback on whether the CPR quality meets the standard or determined limit can be provided by evaluating whether the area index $AreaIndex_{CPR}$ falls within the distribution range. Feedback on whether the CPR quality meets the standard or determined limit can also be provided according to the fluctuation of the area index $AreaIndex_{CPR}$. The feedback flow as shown in FIG. 8*a* can include the following steps 30-39.

In step 30, distribution range limits of the area index $AreaIndex_{CPR}$ can be obtained (the distribution range limit may be related to the required CPR implementation quality) so as to determine a distribution range of the $AreaIndex_{CPR}$ index. This distribution range represents that, if the area index $AreaIndex_{CPR}$ falls within this range, the CPR implementation effect can be regarded as acceptable and therefore the CPR implementation reached the standard or determined limit. These distribution range limits can be input in every CPR implementation, or they can be pre-stored in the system and read from the memory address in every CPR implementation.

Among the normal population, the distribution range of the stroke volume is about 4.8-8 L/min. After the cardiopulmonary function of human body has stopped, as mentioned above, the human body environment is often relatively consistent. About ⅓-¼ of the normal stroke volume can be reached by performing the CPR.

In step 31, the single area index $AreaIndex_{CPR}$ obtained through calculation can be processed to generate the waveform data of the single area index $AreaIndex_{CPR}$. Such a waveform may be displayed on the display interface. The distribution range limits may also be displayed with the waveform of the area index $AreaIndex_{CPR}$ so that the distribution range and the waveform of the area index $AreaIndex_{CPR}$ can be shown in a visual mode as shown in FIG. 9. The distribution range of the area index $AreaIndex_{CPR}$ can be determined by the maximum value ("Max") and the minimum value ("Min").

In step 32, the single area index $AreaIndex_{CPR}$ can be compared with Min so as to evaluate whether the index reaches the standard or determined limit. If the single area index $AreaIndex_{CPR}$ is larger than Min, it may be concluded that the index reaches the standard or determined limit, and then step 33 can be performed. Otherwise, the single area index $AreaIndex_{CPR}$ continues to be compared with Min.

In step 33, a fluctuating value of the area index $AreaIndex_{CPR}$ may be calculated. In order to obtain the fluctuating value of the area index $AreaIndex_{CPR}$, the difference between the area indexes $AreaIndex_{CPR}$ of two adjacent single pulse waves can be calculated.

In step 34, whether the fluctuating value of the area index $AreaIndex_{CPR}$ is less than a second preset value can be evaluated. If so, it may be concluded that the value of the area index $AreaIndex_{CPR}$ is stable and step 35 can be performed. Otherwise, it may be concluded that the value of the area index $AreaIndex_{CPR}$ is unstable and step 36 can be performed.

In step 35, when the fluctuating value of the area index $AreaIndex_{CPR}$ is less than the second preset value, a second prompt message may be outputted. The second prompt message may be used to inform the user that the present compression quality has reached the standard or determined limit. The second prompt message may inform the user that the fluctuating value of the present area index $AreaIndex_{CPR}$ is stable, or the present stroke volume is stable, or the present compression quality (which for example may include some indexes such as compression frequency and compression depth) has reached the standard or determined limit.

In step 36, when the fluctuating value of the area index $AreaIndex_{CPR}$ is equal to or greater than the second preset value, another prompt message may be outputted which can be used to inform the user that the present compression quality fails to reach the standard, or no prompt message is outputted.

In practical CPR applications, the medical staff may, according to the $AreaIndex_{CPR}$ index (reasonable interval of the blood oxygen waveform area), make adjustment(s) to the compression depth and the compression frequency under the precondition of complying with the specifications of the guideline, thus ensuring that the CPR implementation effect falls within the acceptable range, for example, the quantitative indexes of the CPR implementation meet the acceptable range. During such adjustment(s), the medical staff may also search for the maximum value of the $AreaIndex_{CPR}$ parameter and evaluate whether or not the $AreaIndex_{CPR}$ parameter has some significant variations or remains substantially unchanged so as to obtain the optimized CPR implementation effect. For example, if the $AreaIndex_{CPR}$ parameter does not have notable variations after adjusting the depth and the frequency, it may be concluded that an optimal CPR effect has already been achieved.

Additionally, if a CPR instrument is used to deliver compressions, some result information can be outputted to the CPR instrument, allowing it to auto-regulate. Step 37 may be performed after step 35.

Furthermore, in order to evaluate whether the CPR quality has reached an acceptable state, when the fluctuating value of the area index $AreaIndex_{CPR}$ is less than the second preset value, a third result information may be outputted in step 35 to a CPR instrument with self-regulation of compression. Step 37 may be performed after step 35.

In step 37, adjustment(s) made on the compression depth can be made based on the third result information. For example, the compression depth may be increased slightly.

In step 38, the area index $AreaIndex_{CPR}$ after increasing the compression depth can be calculated and a determination of whether the area index $AreaIndex_{CPR}$ has reached its maximum value can be further evaluated. For example, whether the area index $AreaIndex_{CPR}$ increases with the increase of the compression depth can be evaluated. If so, it may be concluded that the present area index $AreaIndex_{CPR}$ has not reached its maximum value. On the other hand, if the area index $AreaIndex_{CPR}$ does not increase with an increase in compression depth, it may be concluded that the present area index $AreaIndex_{CPR}$ has reached its maximum value. When the present area characteristic is at the maximum value, step 39a can be performed; otherwise, step 39b may be performed.

In step 39a, a fifth result information can be outputted, where the fifth result information may be used to control the CPR instrument in a manner to maintain the present compression depth. A third prompt message can also be outputted, where the third prompt message may be used to inform the user that the test subject has reached an optimal compression state of stroke volume.

In step 39b, a fourth result information may be outputted, which can be used to control the CPR instrument to increase the compression depth appropriately or find other causes.

In addition, if the fluctuating value of the area characteristic is less than the second preset value but fails to fall within the area distribution range, a second result information can be outputted, and the CPR instrument may be commanded to increase the compression depth based on the second result information.

Figure 9A:
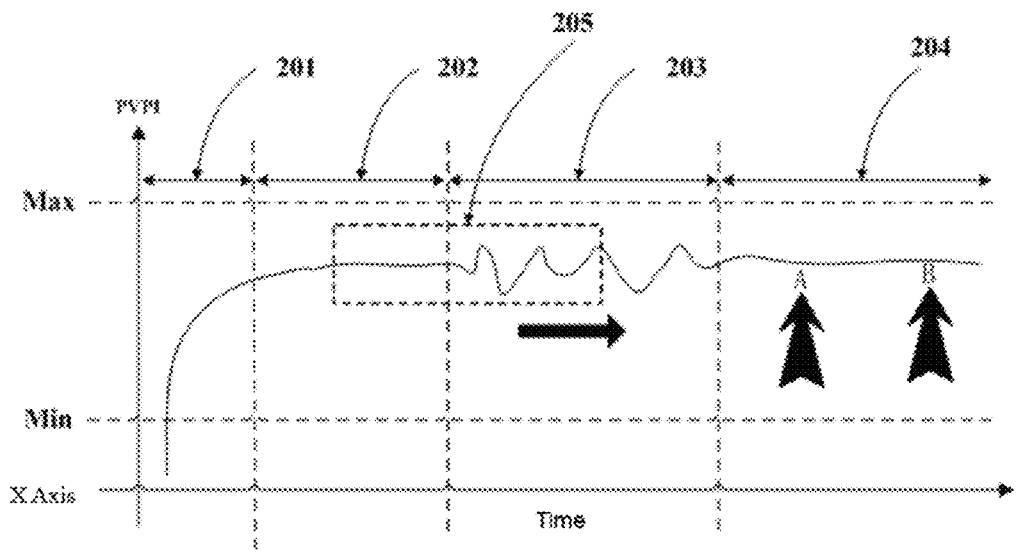
FIG. 9a is a schematic diagram showing a distribution range and a waveform of an area index in visual mode according to an embodiment of this disclosure.

To observe the waveform graph of the area index $AreaIndex_{CPR}$ in a more visual manner, marks can also made at various wave stages on the waveform graph. For example, as shown in FIG. 9a, the rising stage 201, the stable stage 202, the unstable stage 203 and the adjustment stage 204 can be distinguished by partition markings. When evaluating whether the value of the area index $AreaIndex_{CPR}$ is stable, a sliding time window 205 may be used, where the fluctuation characteristic of the index parameter value in the time window 205 can be measured. For example, whether the area index $AreaIndex_{CPR}$ in the sliding time window 205 is stable can be evaluated. In this figure, the rising stage 201 shows the unstable state of the area index $AreaIndex_{CPR}$ in rapid variation at the beginning of a compression; the stable stage 202 shows the state with relatively good CPR quality; while the unstable stage 203 shows the state with relatively poor CPR quality. When CPR is relatively stable, adjustment(s) can be made to the compression depth to find the individual maximum cardiac output. At the adjustment stage 204, the value of the area index $AreaIndex_{CPR}$ may enter a stable stage. At this stage, the medical staff may make further adjustment(s) to the compression depth. For example, the compression depth can be adjusted from about 5 cm at point A to about 6 cm at point B. It can be found that, A and B have a consistent influence effect on the parameter index. Thus, it may be concluded that the maximum cardiac output has been achieved under a compression of about 5 cm. The medical staff may evaluate whether an optimal compression state of the stroke volume has been achieved through a visual diagram. In addition, the system may also output some prompt message to alert the medical staff. For example, when the present area characteristic is at the maximum value, the system may maintain the present compression depth and output the third prompt message, where the third prompt message can be used to inform the user that the test subject has reached an optimal compression state of the stroke volume.

For the amplitude characteristic, the feedback processing described in steps 30-39 can also be used. That is, the mapping value of amplitude characteristic corresponding to "compression depth ≥5 cm" can be first established, which mapping value constitutes an amplitude distribution range limit. On the display interface, the system may display the waveform graph of the amplitude characteristic and the amplitude distribution range limit related to the standard value of cardiac compression depth on the waveform graph, thereby showing a distribution range of the amplitude characteristic in visual mode. By observing whether the amplitude characteristic falls within the amplitude distribution range limit, the medical staff may evaluate whether the compression depth reaches the standard or determined limit.

Figure 8B:
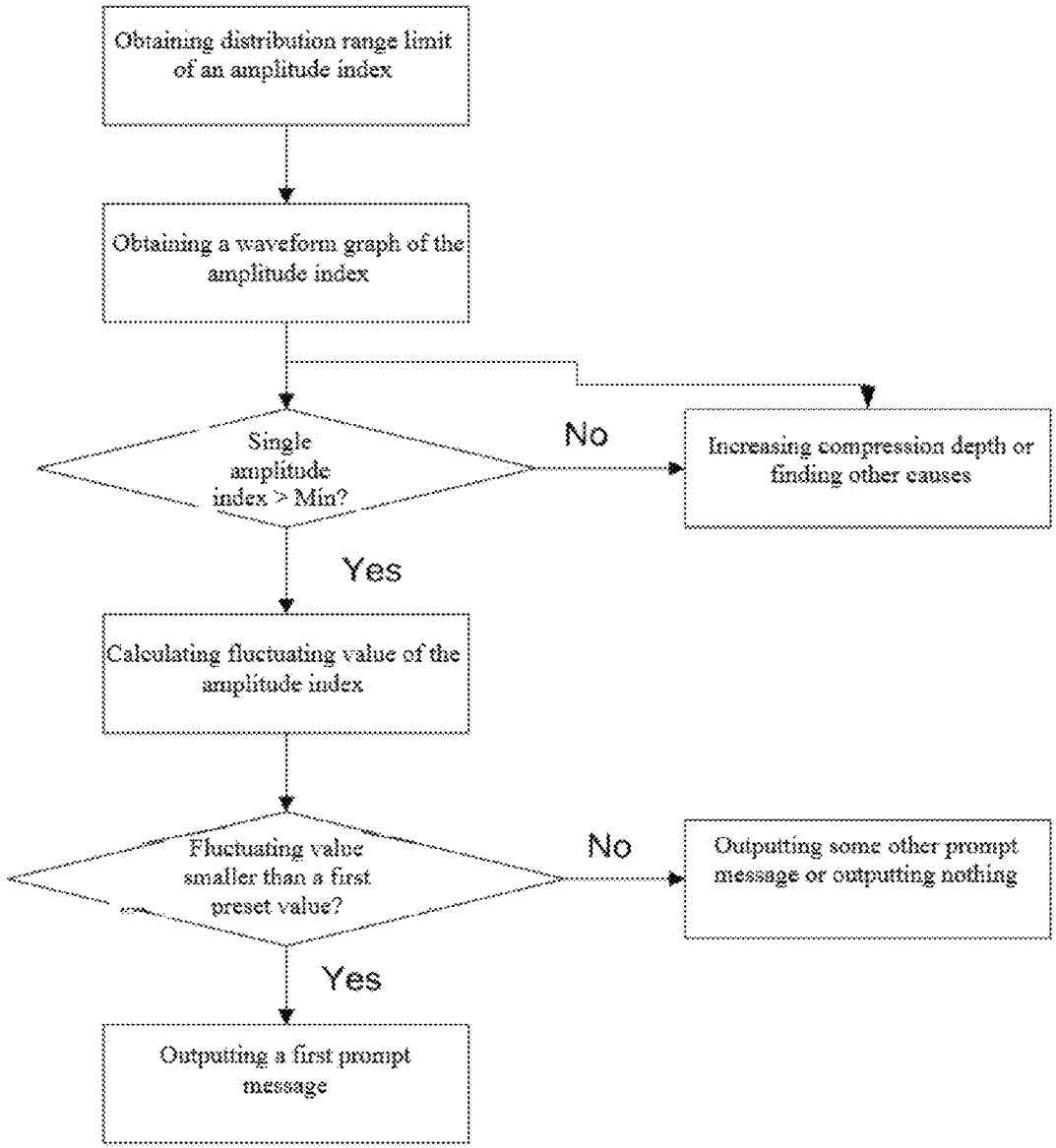
FIG. 8b is a flow chart of providing pulse oximeter-based feedback on peripheral circulation parameters according to another embodiment of this disclosure.

In the embodiment shown in FIG. 8b, the fluctuating value of the amplitude characteristic can be calculated according to the amplitude characteristic of a single pulse wave, and then whether the fluctuating value of the amplitude characteristic is less than the first preset value and whether the amplitude characteristic falls within the amplitude distribution range limit can be evaluated. If so, the system may output the first prompt message, where the first prompt message can be used to inform the user that the present compression depth has reached the standard or determined limit. If the fluctuating value of the amplitude characteristic is less than the first preset value but the amplitude characteristic does not fall within the amplitude distribution range limit, the system may output the first result information, and command the CPR instrument to increase the compression depth based on the first result information.

Figure 9B:
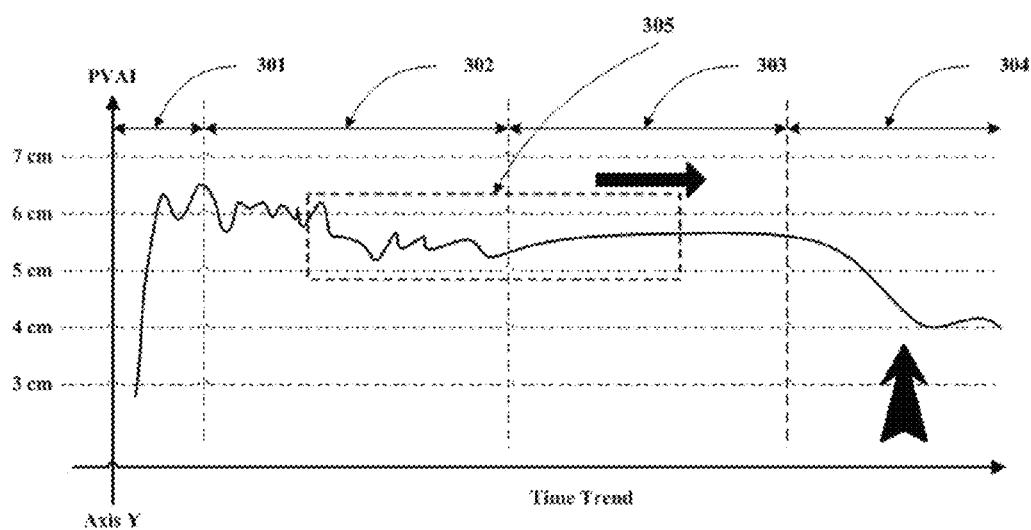
FIG. 9b is a schematic diagram showing a waveform of an amplitude index in visual mode according to an embodiment of this disclosure.

To observe the waveform graph of the amplitude index in a more visual manner, marks can also be made at various wave stages on the waveform graph. For example, as shown in FIG. 9b, the rising stage 301, the unstable stage 302, the stable stage 303 and the alarm stage 304 may be distinguished by partition marking. As shown in FIG. 9b, a sliding time window 305 can be established and the fluctuation characteristic of the index parameter value in the time window 305 can be measured. The rising stage 301 in this figure shows the rapid variation of the index parameter at the beginning of compression. If there is significant fluctuation as shown by the unstable stage 302 in the figure, the system may indicate that the compression depth is unstable and the compression state should be adjusted. If the index parameter values shown by the stable stage 303 are stable with a difference not exceeding about ±5% (±5% refers to the proportion of the D-value of fluctuations in the average value in the time window, which can be independently adjusted according to actual needs), it may be concluded that the compression depth is stable. According to the specifications of CPR guidelines, the compression depth should be at least about 5 cm. If the mean compression depth in the sliding time window is less than the limit corresponding to about 5 cm, the system can display the alarm stage 304 and warn the medical staff to increase the compression depth.

Frequency domain analysis method is used to process the data in another embodiment, which can be the difference between this embodiment and the above-described embodiments.

Figure 10:
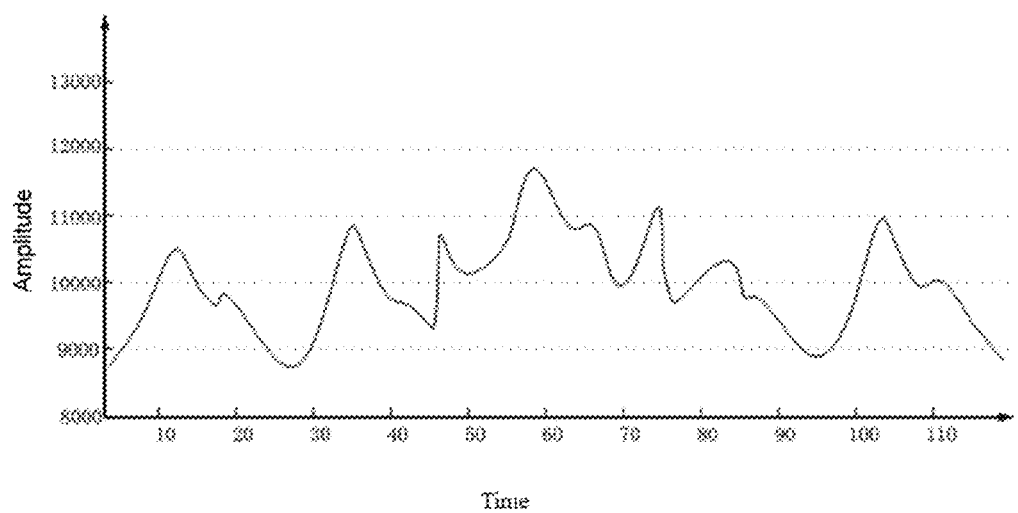
FIG. 10 shows a waveform of a fluctuant component including interference factors according to an embodiment of this disclosure.

During CPR, there may be many interference factors such as the vibrations generated by a compression, the vibrations of chest cavity, and the impact of medical devices. In FIG. 10, an example of the waveform graph of the separated fluctuant component is shown. Due to these factors, the parameters obtained by the above-described method may be distorted. Since there can be energy conservation for the signal between a domain and its corresponding transform domain as demonstrated in formula 6 (below), those above-described parameters should be established based on the frequency domain analysis technique.

$$\sum_{n=0}^{N-1} |S_{AC}(n)|^2 = \frac{1}{M} \sum_{k}^{M-1} |X(k)|^2 \quad (7)$$

where X(k) represents the amplitude value of each frequency spectrum component, and M represents the M frequency spectrum components existing in the frequency spectrum.

Figure 11:
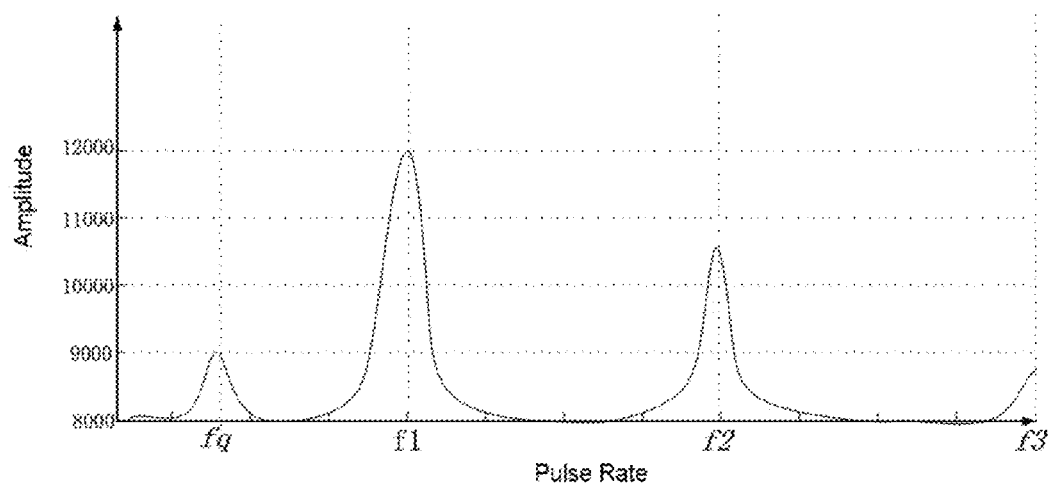
FIG. 11 is a diagram illustrating a spectral distribution of blood oxygen signals acquired using the frequency domain analysis method according to an embodiment of this disclosure.

Spectrum analysis can be performed on the blood oxygen signal to obtain a spectral distribution diagram. As shown in FIG. 11, the frequency $f_1$ is the main frequency or the fundamental frequency and is consistent with the CPR compression frequency. In addition to the main frequency, there may be several double frequencies. For example, $f_2$ and $f_3$ are double frequencies in FIG. 11. These main and double frequencies are referred to as the effective frequency components of the signal. As shown in FIG. 11, fq is the interfering frequency. In this embodiment, formula (6) can be used to calculate the signal frequency spectrum at the positions of the effective frequency components (including the main frequency $f_1$ and the double frequencies $f_2, f_3 \ldots f_N$) so as to obtain the corresponding evaluation indexes. For an uninterrupted steady signal, the effective value of the signal calculated through the time domain method should be equal to that calculated through the frequency domain method. However, in real applications, the frequency domain method often has better anti-interference capacity.

In one embodiment, the frequency domain analysis method can be used to calculate the blood oxygen frequency characteristic as well as the amplitude characteristic and the area characteristic of a single pulse wave.

The blood oxygen frequency characteristic of the pulse oximetry waveform can be calculated. $f_1$ represents the main frequency of the fluctuant component of $S_{AC}$ and this frequency is consistent with the CPR compression frequency. When this frequency is multiplied by 60, the result is the blood oxygen frequency characteristic, namely CPR compression degree/min.

$$F^*_{CPR} = f_1 \quad (8)$$

$$\text{Deg}^*_{CPR} = F^*_{CPR} * 60 = f_1 * 60 \quad (9)$$

where $F^*_{CPR}$ represents the CPR compression frequency, $f_1$ represents the signal frequency, and $\text{Deg}^*_{CPR}$ represents the CPR compression degree/min with a unit of times per minute.

In clinical CPR application, whether the CPR compression frequency is stable can be evaluated by observing the stability of $\text{Deg}^*_{CPR}$ index or pulse rate parameter. Under the precondition of complying with the specifications of the guideline, manual operation or automation device can be used to adjust the CPR compression frequency. In general clinical applications, when the compression frequency is at least about 100 degrees/min, it may be concluded that the compression frequency quality has reached the standard or determined limit (this index can be modified according to a large amount of data collected on practical clinical applications).

The amplitude characteristic of single pulse wave of a pulse oximetry waveform can be calculated based on the effective frequency component of the fluctuant component of $S_{AC}$, so as to evaluate the variations of the compression depth in the CPR implementation process. This amplitude characteristic can be calculated by using any suitable techniques, such as maximum amplitude selection method (max amplitude), average amplitude selection method (average amplitude), or root mean square method (root mean square). In one embodiment, the root mean square method may be used to extract the absolute amplitude value $\text{Amp}^*_{CPR}$ of all the frequency components $f_n$ (n=1, 2, 3, . . . N) of the fluctuant component of $S_{AC}$. The corresponding formula is as follows:

$$\text{Amp}^*_{CPR} = \sqrt{\frac{\sum_{n=0}^{N-1} \left( \sum_{k=0}^{K-1} X_{f_n}(k)^2 \right)}{K}} \quad (10)$$

where $\text{Amp}^*_{CPR}$ represents the absolute amplitude value, k represents the sampling data point of the current $f_n$, K represents the total data length of the effective main frequency $f_n$, and n represents the $n^{th}$ frequency peak which amounts to N effective frequency peaks.

In other examples, the amplitude characteristic of the main frequency $f_1$ can also be used to evaluate the variations of the compression depth in the CPR implementation process. Amp*$_{CPR}$ can reflect the depth variation in the CPR compression process. In theory, Amp*$_{CPR}$ should exhibit linear dependence with the compression depth. When the compression depth is stable, the parameter value of Amp*$_{CPR}$ should be stable with less fluctuations. In clinical CPR application process, the compression depth may be unstable at the beginning stage, in which case the index value of Amp*$_{CPR}$ may also be unstable with significant fluctuations. With the stabilization of the compression depth, the index value of Amp*$_{CPR}$ can become relatively stable. In clinical applications, the CPR guidelines specify that the compression depth should be at least about 5 cm. In some embodiments, corresponding relations can be established between Amp*$_{CPR}$ and the compression amplitude according to a series of animal and human experiments, thereby providing a mapping value of Amp*$_{CPR}$ when the compression depth is at least about 5 cm. After Amp*$_{CPR}$ is calculated, Amp*$_{CPR}$ can be compared with the mapping value. If Amp*$_{CPR}$ is stable in fluctuation and comparable with this mapping value, it may be concluded that the compression depth has reached the standard or determined limit (this index can be modified based on future clinical data results).

In order to evaluate the variations of the stroke volume in the CPR implementation process and indirectly reflect the CPR implementation quality, the area characteristic of a single pulse wave of the pulse oximetry waveform can be calculated based on the effective frequency components of the fluctuant component of $S_{AC}$. Any suitable techniques, such as area integral method (continuous signal and discrete signal), can be used to calculate the area characteristic to obtain the area information of each pulse wave. In this embodiment, since the sampling frequency is fixed in the blood oxygen technology, the method of point-by-point accumulation integral may be used to calculate the absolute area value Area*$_{CPR}$.

$$\text{Area}^*_{CPR} = \sum_{n=0}^{N-1} \left( \sum_{k=0}^{K-1} X_{f_n}(k) \right) \quad (11)$$

where Area*$_{CPR}$ represents the absolute area value of single pulse wave which corresponds to the parameter related to the stroke volume and is also referred to as voltage volume, n represents the current effective frequency component $f_n$, N represents the total number of the effective frequency components, k represents the sampling data point of the current effective frequency $f_n$, and K represents the total data length of the effective frequency component $f_n$.

Area*$_{CPR}$ can be used to indirectly reflect the stroke volume. In theory, Area*$_{CPR}$ should exhibit linear positive correlation with the cardiac ejection volume in every compression. When the compression depth is stable and the compression frequency is constant, the parameter value of Area$_{CPR}$ should be stable with small fluctuations. In clinical CPR application process, the compression depth and the compression frequency may be unstable at the beginning stage, and thus the outputted index value of Area*$_{CPR}$ may also have large fluctuations, namely a large variation range of index values. When the compression depth and the compression frequency are stable, the index values of Area*$_{CPR}$ should also exhibit relatively stable characteristics, namely the variations in index value should fall within a relatively small range of fluctuations. Once this happens, the stroke volume may have reached its maximal output limit. When the compressions have reached this point, the stroke volume may not be improved by increasing the depth and the frequency. According to this characteristic, when Area*$_{CPR}$ is in a relatively stable state, the medical staff may make adjustment(s) to the depth and the frequency and then observe the variations of Area*$_{CPR}$ parameter index. If the parameter value changes slightly (for example, the variation is less than or equal to about 10%, 5% or any other value set according to practical clinical considerations) or fails to notably increase with the increase of the compression depth, it may be concluded that Area*$_{CPR}$ has reached the maximum value.

In some embodiments, when applying the frequency domain analysis method for data processing, the amplitude index AmpIndex*$_{CPR}$ of a single pulse wave and the area index AreaIndex*$_{CPR}$ of a single pulse wave can be calculated after amplifying/reducing the blood oxygen signals. The calculation formula is as follows:

$$\text{AmpIndex}^*_{CPR} = \frac{\sqrt{\sum_{n=0}^{N-1} \left( \sum_{k=0}^{K-1} X_{f_n}(k)^2 \right)}{K}}{\left( \sum_{n=0}^{N-1} S_{DC}(n) \right) / N} \quad (12)$$

where Ampindex*$_{CPR}$ represents the amplitude index of a single pulse wave, which is a ratio between the absolute amplitude value of a single pulse wave and the corresponding DC component.

AmpIndex*$_{CPR}$ is a quantization parameter. This parameter can reduce or eliminate the influence of the amplification on the signal amplitude, have sound anti-interference capacity, and visually reflect the variations of the compression depth.

$$\text{AmpIndex}^*_{CPR} = \frac{\text{Area}^*_{CPR}}{\left( \sum_{n=0}^{N-1} S_{DC}(n) \right) / N} = \frac{\sqrt{\sum_{n=0}^{N-1} \left( \sum_{k=0}^{K-1} X_{f_n}(k) \right)}{K}}{\left( \sum_{n=0}^{N-1} S_{DC}(n) \right) / N} \quad (13)$$

where AreaIndex*$_{CPR}$ represents the area index of a single pulse wave, which is a ratio between the absolute area value of a single pulse wave and the corresponding DC component.

AreaIndex*$_{CPR}$ is a quantization parameter. It may reduce or remove the individual difference and the interference caused by signal amplification/reduction and have sound anti-interference capacity.

The above-described steps 31-39 are also applicable to the following embodiment. When adopting the frequency domain analysis method, the CPR quality can be reflected by the area index and its fluctuation.

In some embodiment, after the fluctuant components are separated from the acquired blood oxygen signals, a pulse waveform including one or more single pulse wave(s) can be generated based on the fluctuant components (step 102). The one or more single pulse wave(s) may further be recognized for compression interruption monitoring during the CPR process (step 104).

In the case where the patient has no restoration of spontaneous circulation, cardiac impulse and thus blood circulation at finger tips may be generated by compressing the patient's heart. Once stopping cardiac compression, the blood circulation may disappear correspondingly. That is, the pulse wave can be generated under compression, and the pulse wave may disappear after stopping compression. Therefore, manual/mechanical compression state can be recognized from the pulse wave based on its changes following the compression. The manual/mechanical compression state herein can include a continuous compression state in which there is continuous pulse wave signal and a compression interruption state in which the pulse wave may disappear, where the continuous compression state and the compression interruption state may also be called as a pulse state and a pulseless state.

The pulse wave can be recognized based on amplitude and width of a single pulse wave. The amplitude as described above can be defined as the AC component, while the width may correspond to a mapping value of the sampling point count of a single pulse wave. The mapping relation among the sampling point count, the pulse width, and the pulse rate may be defined as follows:

$$\text{PulseRate}=60 * f_{HZ} = 60 * \text{SampleRate/Width} \quad (14)$$

where PulseRate represents a pulse number per minute (degree/min), $f_{HZ}$ represents the frequency of a single pulse wave, SampleRate represents a sampling rate for blood oxygen signal, and Width represents a pulse width for a single pulse wave (i.e., the sampling point count). The area index in the time domain can then be obtained based on the width of the single pulse wave.

Typically, the amplitude information and the width information of one single pulse wave may be extracted for evaluating whether the single pulse wave is complete. During clinical emergency treatment, it may become more difficult to accurately recognize the pulse wave based on the amplitude information and the width information of one single pulse wave due to some environmental interference.

In one embodiment, multiple single pulse waves may be used for pulse wave recognition, where a disappearing period of the pulse wave may be recognized based on changes of multiple single pulse waves. In one embodiment, at least three continuous single pulse waves can be extracted, and then the disappearing period of the pulse wave can be recognized based on area variation and/or shape variation of these single pulse waves.

For the purpose of improving the accuracy in recognizing the pulse wave, more characteristic information can be utilized for auxiliary recognition. In one embodiment, area fluctuation and/or shape relevance among multiple continuous single pulse waves (e.g., about three) can be used to improve the recognition of the pulse and/or pulseless state significantly, thereby reducing the influences from some clinical interference.

In a following step 106, the disappearing period of the pulse wave can be counted based on the recognition result, where such disappearing period may correspond to a manual/mechanical compression interruption period. Subsequently, the counting information can be outputted in step 108. For example, the counting information can be displayed on a display screen.

For the counting operation in step 106, duration of the disappearing period of the pulse wave (also called disappearing duration) can be calculated in one embodiment, and/or a total time percentage of the disappearing period of the pulse wave (also called total time percentage of disappearing duration) can be calculated in another embodiment. The total time percentage of the disappearing period of the pulse wave may refer to a ratio between the accumulated duration of the disappearing period of the pulse wave and the duration of the CPR operation (also called CPR duration).

In another embodiment, in addition to counting the disappearing duration of the pulse wave, the compression period in which the pulse wave can be generated (also called compression duration) can also be counted. This compression period refers to an appearing period of the pulse wave. In this case, when multiple single pulse waves are used for pulse wave recognition, the compression period in which the pulse wave can be generated/detected may also be recognized based on changes of multiple single pulse waves. Duration of the compression period and/or a total time percentage of compression duration can be calculated.

In another embodiment, the counting step may further include presetting a first threshold and a second threshold, and prompting warning information when the disappearing duration exceeds the first threshold and/or when the total time percentage of disappearing duration exceeds the second threshold.

A total duration, i.e. the duration of the CPR operation, can be counted through the following methods in this disclosure. Under default settings, the time-counting operation may be started once the patient wears the blood oxygen probe and the CPR duration may be reset when the blood oxygen probe is not connected to the patient (the blood oxygen probe is used for acquiring physiological signals from the patient). Alternatively, a start button and a stop button can be provided, and the time-counting operation may be started and stopped respectively by a medical staff clicking on the start button and the stop button.

At the end of the manual/mechanical compression interruption period, the manual/mechanical compression state may change into the continuous compression state, and the disappearing duration may be stopped to be counted since the compression waveform can be generated once again.

In one embodiment, the total time percentage of the disappearing period of the pulse wave can be calculated by a following formula:

$$\text{Interval}_{Ratio}^{CPR} = \frac{\sum_{p=1}^{P} \sum_{q=1}^{Q} \text{Interval}(p, q)}{\sum_{n=1}^{N} CPR_{course}(n)} * 100\% \quad (15)$$

where $\sum_{n=1}^{N} CPR_{course}(n)$ represents an accumulated sampling point count during manual/mechanical compression, and $$\sum_{p=1}^{P} \sum_{q=1}^{Q} \text{Interval}(p, q)$$

represents an accumulated sampling point count within a manual/mechanical compression interruption period present in the manual/mechanical compression process (p=1, 2, 3, . . . P, and q=1, 2, 3, . . . Q, where p represents a $p^{th}$ manual/mechanical compression interruption period, P represents a total number of manual/mechanical compression interruption periods present in the manual/mechanical compression process having a length of N points, q represents a $q^{th}$ point during the $p^{th}$ CPR interruption period, and Q represents a total point count of the $p^{th}$ manual/mechanical compression interruption period).

In an embodiment, the compression duration can be obtained by subtracting the disappearing duration from the CPR duration. In an embodiment, the total time percentage of compression duration (Compression$_{Ratio}^{CPR}$) can be determined by: 1−Interval$_{Ratio}^{CPR}$. In another embodiment, the counting step may further include presetting a third threshold and prompting further information when the total time percentage of compression duration is smaller than the third threshold.

Based on the accurate recognition of the single pulse wave signal, sliding time window can be used to recognize the manual/mechanical compression state in another embodiment.

Figure 23:
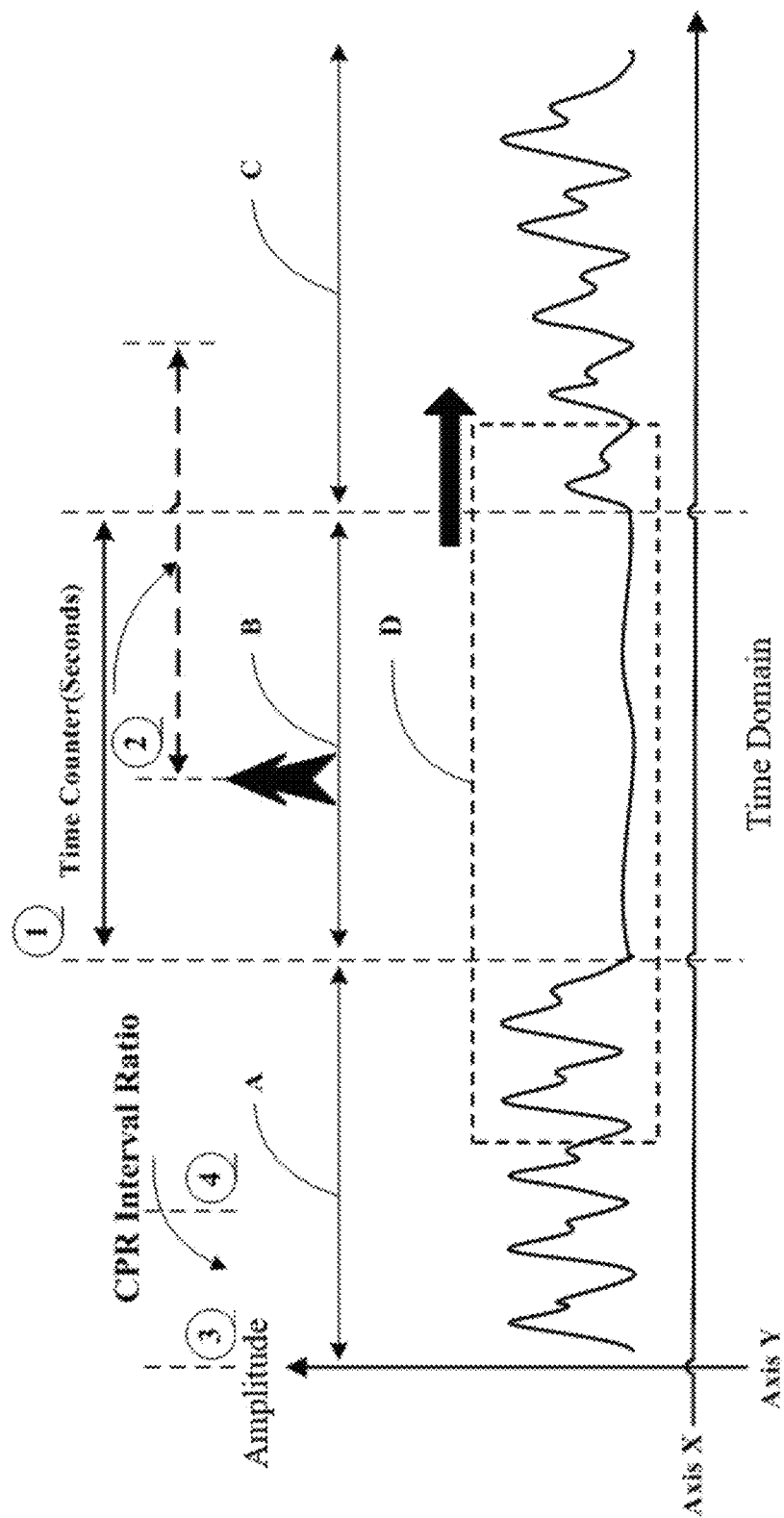
FIG. 23 shows variations of a manual/mechanical compression state according to an embodiment of this disclosure.
Figure 24:
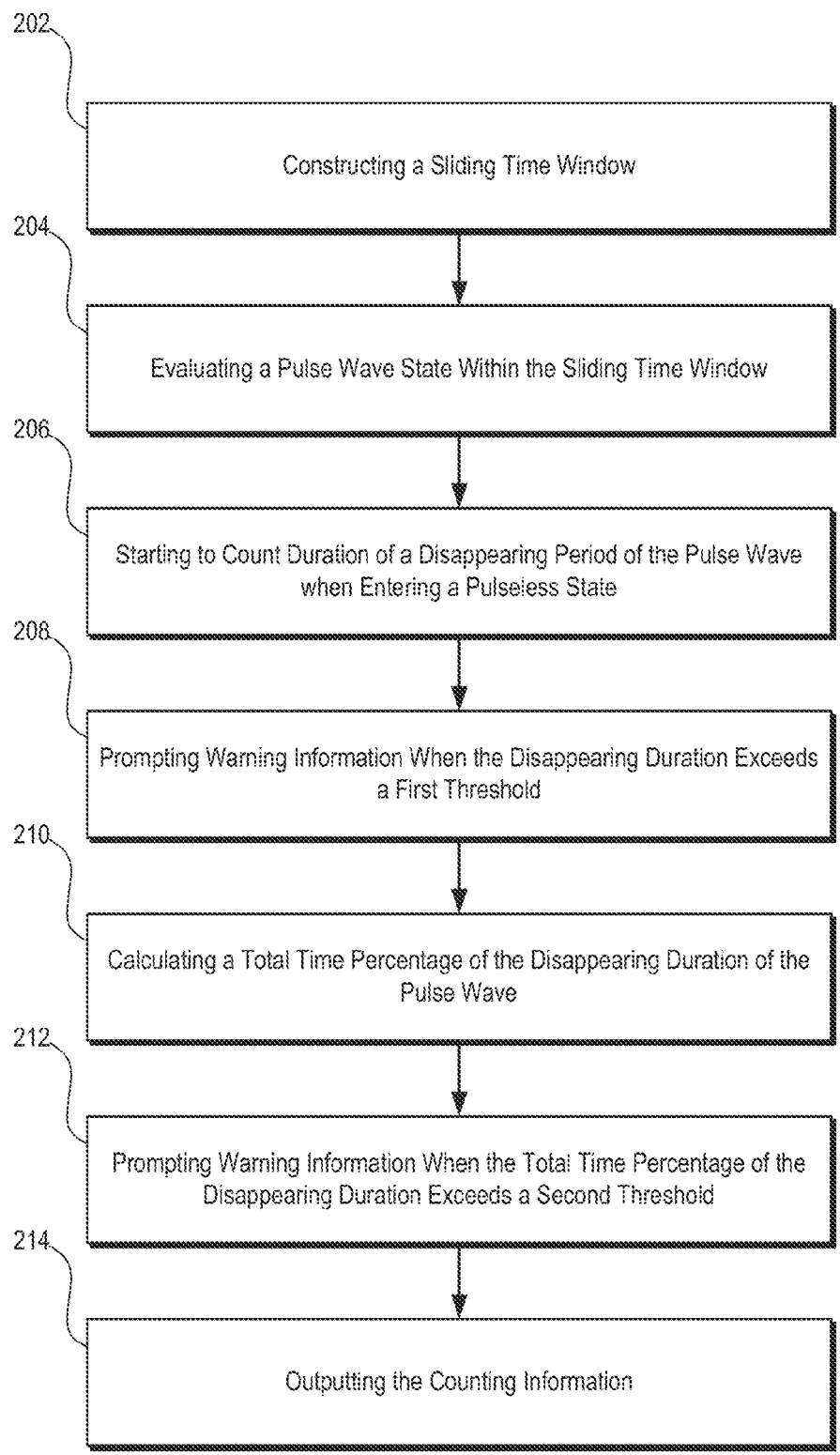
FIG. 24 is a flow chart for monitoring a compression interruption period during the CPR process according to another embodiment of this disclosure.

In step 202, a sliding time window shown by D in FIG. 23 can be constructed so as to observe a pulse wave state within this window. Duration of the sliding time window can be set according to an actual situation. For instance, its duration can be about 10 s in default setting.

In step 204, the pulse wave state within the sliding time window can be evaluated, and some other operations may be triggered based on the evaluation result. In view of response speed and stability, feature recognition can be performed on about three pulse waves, so as to determine whether the current manual/mechanical compression state is the manual/mechanical continuous compression state or the manual/mechanical compression interruption state. As shown in FIG. 23, after performing the feature evaluation on about three pulse waves, the pulse waves in the section A (i.e., CPR Duration 1) and the section C (i.e., CPR Duration 2) can be determined to be generated by manual/mechanical compression and thus the time counting may not be started for the disappearing period of the pulse wave in these two states.

In step 206, the time counting can be started for the disappearing period of the pulse wave once the sampled signals enter a pulseless state. Specifically, the disappearing duration can be counted by accumulating the sampling point count, while the sampling rate within one single period may correspond to about one second. Therefore, the disappearing duration (i.e., duration of the manual/mechanical compression interruption period) can be counted by seconds. In FIG. 23, the time counting for the CPR compression interruption period may be started from the position 1 in section B (i.e., an interval without CPR), and then the time-counting information can be sent to a client. When the manual/mechanical compression interruption period ends, the compression waveforms can be detected once again, the time counting and displaying operations for the CPR compression interruption period can be stopped and the disappearing duration may be reset.

In clinical applications, since the feature evaluation is implemented on about three pulse waves, the sampled data corresponding to the about three pulse waves may be needed for recognizing whether the sampled data is pulseless data and for evaluating whether the current manual/mechanical compression state has changed into the manual/mechanical compression interruption state based on the recognition result when the current state changes into the pulseless state. This may lead to time delay in the time counting & displaying functions for the manual/mechanical compression interruption period. For that reason, when the manual/mechanical compression state changes from the compression interruption state into the continuous compression state, the time counting and displaying functions for the manual/mechanical compression interruption period may last for a certain time before being stopped and reset due to the pulse wave recognition method used in this disclosure. As shown in FIG. 23, the duration of the manual/mechanical compression interruption period may be shown at the position 2 instead of the position 1. Similarly, when entering section C, the duration of the CPR interruption period may still be displayed until about three pulse waves are detected.

The time delay of the time counting and displaying functions for the manual/mechanical compression interruption period may depend on the width of the recognized pulse wave (i.e., pulse rate). The higher the pulse rate is, the shorter the recognition time becomes, and vice versa. When using about three pulse waves in this disclosure, the response speed for recognizing the manual/mechanical compression interruption period may be about 0.6-9 s since a recognizable physiological pulse wave may have a range of [20-300] BPM (which corresponds to a pulse rate of [0.33-5] Hz):

$$Time_{response} = \frac{3 \text{ Pulse}}{[0.33 \text{ Hz} \sim 5 \text{ Hz}]} = [9 \text{ S} \sim 0.6 \text{ S}] \quad (16)$$

where 3Pulse represents about three pulse periods, and [0.33-5] Hz represents the frequencies of the recognizable pulse width.

According to CPR Guidelines, the compression frequency should be at least 100 degrees/min. Based on the formula described above, the response speed may be about 1.64 s; that is, it may take about 1.64 s to recognize the state of the compression waveform in this disclosure. This response speed can meet the time-sensitive requirements of clinical application, and the compression interruption evaluation can improve both the accuracy during emergency treatment and the survival rate of the patient.

In step 208, warning information may be prompted when duration of the disappearing period of the pulse wave exceeds the first threshold. It is known that the patient may be affected physiologically if the CPR is interrupted for about 10 s. For this reason, the first threshold in this disclosure can be set as about 10 s, so that warning information can be provided when the disappearing duration is larger than 10 s.

In step 210, a total time percentage of the disappearing period of the pulse wave (which corresponds to a total time percentage of CPR interruption period) can be calculated, and warning information can be prompted if the total time percentage of the disappearing duration exceeds the second threshold (step 212). Alternatively, a total time percentage of the compression period in which the pulse wave can be generated/detected may also be calculated. That is, the total time percentages of both the disappearing period and the appearing period of the pulse wave can be considered comprehensively, so as to have higher recognition accuracy and sensitivity. According to CPR Guidelines, if the interruption period accounts for more than 20% of the total emergency time by manual/mechanical compression, the patient cannot be successfully rescued. Therefore, the total time percentage of CPR interruption period $\text{Interval}_{Ratio}^{CPR}$ can be defined in this disclosure to reflect the time percentage feature, where the $\text{Interval}_{Ratio}^{CPR}$ may be calculated according to the following formula:

$$\text{Interval}_{Ratio}^{CPR} = \frac{\sum_{p=1}^{P} \sum_{q=1}^{Q} \text{Interval}(p, q)}{\sum_{n=1}^{N} CPR_{course}(n)} * 100\% \quad (15)$$

where $\sum_{n=1}^{N} CPR_{course}(n)$ represents an accumulated sampling point count during manual/mechanical compression, and $$\sum_{p=1}^{P} \sum_{q=1}^{Q} \text{Interval}(p, q)$$

represents an accumulated sampling point count within a CPR interruption period present in the manual/mechanical compression process (p=1, 2, 3, ... P, and q=1, 2, 3, ... Q, where p represents a $p^{th}$ CPR interruption period, P represents a total number of CPR interruption periods present in the manual/mechanical compression process having a length of N points, q represents a $q^{th}$ point during the $p^{th}$ CPR interruption period, and Q represents a total point count of the $p^{th}$ CPR interruption period).

As described above, the sampling rate may have corresponding relation with respect to the time. When calculating the $\text{Interval}_{Ratio}^{CPR}$, the $$\sum_{p=1}^{P} \sum_{q=1}^{Q} \text{Interval}(p, q)$$

and the $$\sum_{n=1}^{N} CPR_{course}(n)$$

related to the sampling rate should be transformed into time scale. Since the two may have the same sampling rate, the factor for sampling rate transformation can be eliminated from the calculation formula of the $\text{Interval}_{Ratio}^{CPR}$. As a result, the $\text{Interval}_{Ratio}^{CPR}$ is substantially equivalent to the percentage in the time scale and it can reflect the ratio between the CPR interruption period and the total manual/mechanical compression period.

In clinical applications, the $\text{Interval}_{Ratio}^{CPR}$ can be updated dynamically in real time. That is, once the blood oxygen system acquires a sampling point during the rescue process by manual/mechanical compression, the acquired sampling point may be counted to update the $$\sum_{n=1}^{N} CPR_{course}(n),$$

whether the acquired sampling point is obtained during the CPR compression interruption period can be evaluated based on the above-described evaluation method, and the $$\sum_{p=1}^{P} \sum_{q=1}^{Q} \text{Interval}(p, q)$$

can then be updated following the evaluation result. Correspondingly, the total time percentage $\text{Interval}_{Ratio}^{CPR}$ can be updated every one sampling point. In this embodiment, the $\text{Interval}_{Ratio}^{CPR}$ can be updated according to the sampling rate (i.e., it can be updated every one second). In FIG. 23, "CPR Interval Ratio" shows that the $\text{Interval}_{Ratio}^{CPR}$ can be present on the display interface as starting the manual/mechanical compression.

As described above, about three pulse waves may be needed for recognition, so as to evaluate whether the current state is the continuous compression state or the compression interruption state. The $\text{Interval}_{Ratio}^{CPR}$ may thus be displayed with a certain time delay, where for example, the $\text{Interval}_{Ratio}^{CPR}$ in FIG. 23 is actually displayed at the position 4 rather than the theoretical position 3. Typically, the delay time can be set as about 1.64 s.

The total time percentage of the CPR compression interruption period may be continuously displayed during the whole manual/mechanical compression process until the manual/mechanical compression state is reset. In this regard, two methods may be used to reset the total time percentage of the CPR compression interruption period. That is, the total time percentage of the CPR compression interruption period may be reset when the restoration of spontaneous circulation is recognized during the manual/mechanical compression process and/or when a reset mechanism is triggered by manual operation (e.g., clicking on a reset button of a monitoring apparatus).

In step 214, the counting information can be outputted. For example, the counting information such as the duration of the disappearing period of the pulse wave and/or the total time percentage of the disappearing period of the pulse wave can be outputted and displayed on a display screen.

Steps 102-108 and 202-210 are related to the feature evaluation based on the pulse wave recognition in the time domain. Due to energy conservation between the time domain and the frequency domain, such feature evaluation on the pulse wave can also be implemented by a frequency-domain method. The frequency-domain analysis method may depend on the data length. In the event of too large data, the variation tendency of the physiological signals may become too slow; when the data length is too short, the data accuracy may not be high enough to cause invalid frequency-domain analysis. In this disclosure, the data length for each frequency-domain analysis can be set as about 6 seconds in combination of clinical application. In order to follow the variations of the physiological signal rapidly, the frequency-domain analysis may be started every 0.5 seconds.

The width characteristic and the amplitude characteristic of the pulse wave in the time domain may be mapped into signal amplitude and signal width in the frequency domain.

Therefore, an amplitude parameter or an area parameter of a frequency peak can be used to evaluate the disappearing duration and the total time percentage of the disappearing duration during the manual/mechanical compression process. When the CPR compression interruption period is recognized, the frequency-domain analysis may be started every 0.5 seconds, and the amplitude or the area of the frequency peak may decrease gradually. An amplitude threshold or an area threshold can be established, and the current compression state can be deemed to be the manual/mechanical compression interruption period when none of the amplitude values or the area values of one or more frequency peak (e.g., about four) is higher than the corresponding threshold.

The duration of the manual/mechanical compression interruption period may also be displayed after a certain time delay, where the delay time may depend on an interval and the number of the respective frequency-domain analysis. As mentioned above, since the interval of the respective frequency-domain analysis may be about 0.5 seconds and the frequency-domain analysis may be performed for four times, the delay time in the frequency domain can be approximately 2 seconds. Here, a minimum resolution of the CPR interruption period may be constrained by the interval of the frequency-domain analysis to be about 0.5 seconds, for example. When the manual/mechanical compression interruption state is recognized, the time counting & displaying operations can be started for the manual/mechanical compression interruption period; when the manual/mechanical continuous compression state is recognized, the time counting operation for the manual/mechanical compression interruption period can be shut down. During the frequency-domain analysis, the total time percentage of the manual/mechanical compression interruption period (i.e., the total time percentage of the CPR compression interruption period) may be calculated once starting the manual/mechanical compression. By performing the frequency-domain analysis every 0.5 seconds, a total duration (i.e., the CPR duration) may be accumulated, a current state is the CPR compression interruption period can be evaluated, and the duration of the CPR compression interruption period can be accumulated. Here, the total time percentage of the CPR compression interruption period may refer to a ratio between the duration of the CPR compression interruption period and the CPR duration, and a minimum resolution of the total time percentage of the CPR compression interruption period may be constrained by the interval of the frequency-domain analysis. The starting and reset mechanisms in the frequency domain can be the same as those in the time domain.

Figure 12:
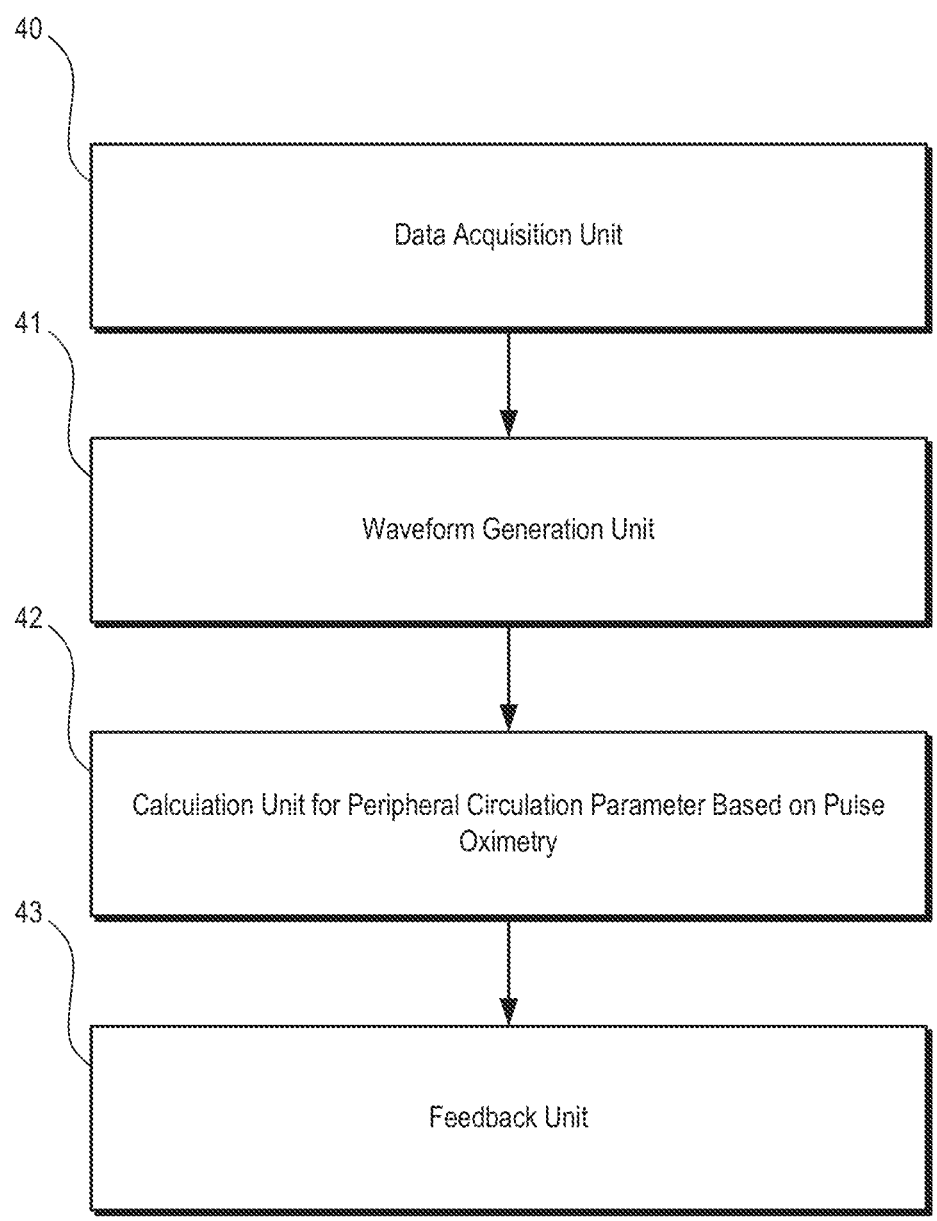
FIG. 12 is a structural diagram of a CPR quality feedback system according to an embodiment of this disclosure.

Based on the above-described methods, the embodiments of this disclosure describe CPR quality feedback systems. As shown in FIG. 12, an example CPR quality feedback system may include a data acquisition unit 40, a waveform generation unit 41, a calculation unit for peripheral circulation parameter related to CPR quality 42 and a feedback unit 43. The data acquisition unit 40 can be used to acquire the blood oxygen signals of the test subject undergoing CPR. The waveform generation unit 41 can be used to generate a pulse oximetry waveform based on the acquired blood oxygen signals. The calculation unit for peripheral circulation parameter related to CPR quality 42 can be used to calculate peripheral circulation parameters related to CPR quality based on the pulse oximetry waveform. The feedback unit 43 can be used to provide feedback on the peripheral circulation parameter related to CPR quality. The peripheral circulation parameters related to CPR quality may include the blood oxygen characteristic of the pulse oximetry waveform and the peripheral circulation parameters generated by compression. The peripheral circulation parameters generated by compression may include the amplitude characteristic of a single pulse wave and/or the area characteristic of a single pulse wave. When providing feedback on the CPR implementation quality, the blood oxygen characteristic and the amplitude characteristic of a single pulse wave can be used to evaluate for CPR quality. The blood oxygen characteristic and the area characteristic of a single pulse wave can also be used to evaluate the CPR implementation quality. Further, the blood oxygen characteristic together with the amplitude characteristic and the area characteristic of a single pulse wave can be used to evaluate the CPR quality. In this embodiment, the last situation using the blood oxygen characteristic as well as the amplitude characteristic and the area characteristic of single pulse wave is described in more detail. In the evaluation process, the amplitude characteristic of single pulse wave may be an absolute amplitude value or an amplitude index; the amplitude index is a ratio between the absolute amplitude value of a single pulse wave of the fluctuant component of amplified/reduced pulse oximetry waveform and the corresponding DC component. The area characteristic of a single pulse wave may be an absolute area value or an area index; the area index is a ratio between the absolute area value of a single pulse wave of the fluctuant component of amplified/reduced pulse oximetry waveform and the corresponding DC component.

Since the original pulse oximetry waveform may contain the constant component and the fluctuant component, the calculation unit for peripheral circulation parameters related to CPR quality 42 can first separate out the constant component and the fluctuant component from the pulse oximetry waveform, then calculate the peripheral circulation parameters generated by the compression based on the fluctuant component of the pulse oximetry waveform, and then calculate the blood oxygen frequency characteristic based on the pulse oximetry waveform or based on the fluctuant component of the pulse oximetry waveform.

In an embodiment, the feedback unit 43 may convert the peripheral circulation parameter related to CPR quality into video information that can be displayed on a display interface, so that parameters (for example: the blood oxygen characteristic, the amplitude characteristic of single pulse wave, and the area characteristic of single pulse wave) appear on the display interface.

In another embodiment, the feedback unit 43 may convert the peripheral circulation parameters generated by compression (such as the amplitude characteristic and the area characteristic of a single pulse wave) into waveform data that can be displayed on a display interface, so as to facilitate the user to observe the variations of the amplitude characteristic and the area characteristic.

Theoretically, the amplitude characteristic should exhibit linear correlation with the compression depth. When the compression depth is stable, the parameter value of the amplitude characteristic should be stable with less fluctuations. In a clinical CPR process, the compression may be unstable at the beginning stage, in which case the index value of the amplitude characteristic are unstable with significant fluctuations. With the stabilization of the compression depth, the index values of the amplitude characteristic can become relatively stable. The area characteristic may exhibit linear positive correlation with the cardiac ejection volume in every compression. When the compression depth is stable and the compression frequency is constant, the parameter values of the area characteristic should be stable with less fluctuations. In a clinical CPR process, the compression depth and the compression frequency may be unstable at the beginning stage, in which case the outputted index values of the area characteristic may also be unstable with significant fluctuations, namely the change range of values is relatively wide. With the stabilization of the compression depth and the compression frequency, the index values of the area characteristic can become relatively stable (i.e., the value variations may be concentrated within a small range of fluctuations). Therefore, the user may evaluate whether the compression depth and the compression frequency are stable by observing the variations of the amplitude characteristic and the area characteristic.

In clinical practice, the compression depth should be greater than or equal to about 5 cm. The amplitude characteristic can directly reflect the compression depth. In such case, if the user can find the mapping value corresponding to the compression depth of about 5 cm and display this value on the waveform graph of the amplitude characteristic, the user can conveniently evaluate whether the compression depth has met the guideline recommendations according to the value of the displayed amplitude characteristic. The corresponding relation between the displayed amplitude characteristic and the compression amplitude can be established according to a series of tests on animal and/or human bodies, and then mapping the value of the amplitude characteristic when the compression depth is at least about 5 cm. This mapping value may constitute the amplitude distribution range limit related to the standard or determined limit value of cardiac compression depth, which can be displayed on the same interface with the amplitude waveform data. When the amplitude characteristic has reached this mapping value with minimal fluctuations, it may be concluded that the compression depth has reached the guideline standard or determined limit. In this embodiment, the compression depth of at least 5 cm is taken as an the reference standard, although this can be modified according to the data on practical clinical applications.

In the case of the waveform graph of the area characteristic, the area distribution range limit related to the standard value of cardiac compression depth and the area waveform data can be displayed on the same waveform graph of the area characteristic. When the area characteristic falls within the area distribution range limit, it may be concluded that the compression depth and the compression frequency have basically reached the standard or determined limit.

Figure 13:
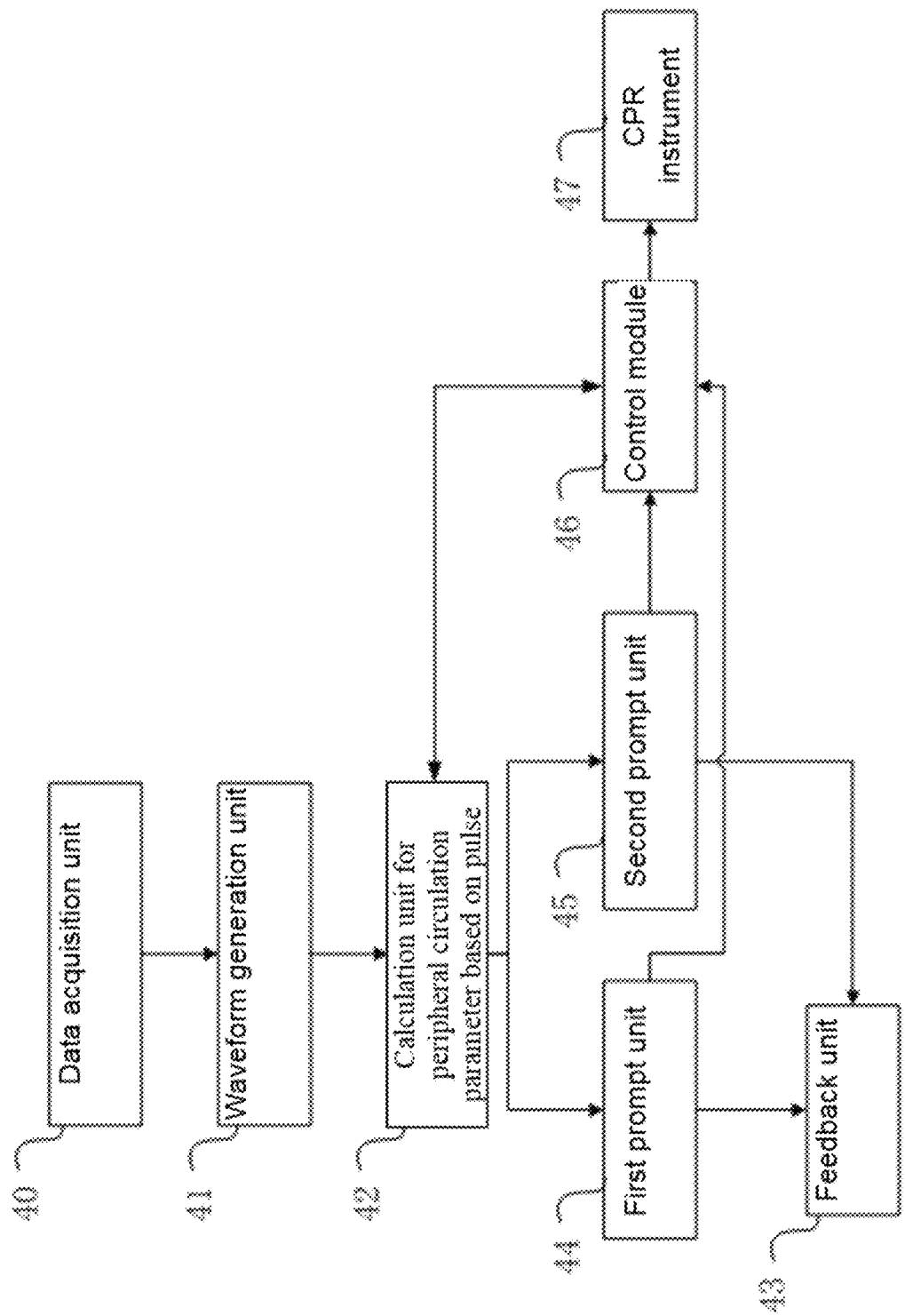
FIG. 13 is a structural diagram of a CPR quality feedback system according to another embodiment of this disclosure.

When evaluating CPR quality, the user may observe the waveform graphs of the amplitude characteristic and the area characteristic. In another embodiment, feedback and control on the CPR implementation quality can also be made by automatic evaluation and prompt adjustments. As shown in FIG. 13, the CPR quality feedback system in this embodiment may include a data acquisition unit 40, a waveform generation unit 41, a calculation unit for peripheral circulation parameter related to CPR quality 42, a feedback unit 43, a first prompt unit 44, a second prompt unit 45 and a control module 46. The data acquisition unit 40, the waveform generation unit 41, the calculation unit for peripheral circulation parameter related to CPR quality 42 and the feedback unit 43 can be the same as those in the embodiment as shown in FIG. 12. The first prompt unit 44 can be used to calculate the fluctuating value of the amplitude characteristic and evaluate whether the fluctuating value of the amplitude characteristic is less than a first preset value and whether the amplitude characteristic falls within the amplitude distribution range limit. If so, the system may output a first prompt message, where the first prompt message can be used to inform the user that the present compression depth has reached the standard or determined limit. The first prompt unit 44 can output a first result information when the fluctuating value of the amplitude characteristic is less than the first preset value but the amplitude characteristic does not fall within the amplitude distribution range limit. The second prompt unit 45 can be used to calculate the fluctuating value of the area characteristic and evaluate whether the fluctuating value of the area characteristic is less than a second preset value and whether the area characteristic falls within the area distribution range limit. If so, the second prompt unit 45 may output a second prompt message, where the second prompt message can be used to inform the user that the present compression quality has reached the guideline standard or determined limit. The second prompt unit 45 can output a second result information when the fluctuating value of the area characteristic is less than the second preset value, but the area characteristic does not fall within the area distribution range limit. The second prompt unit 45 can also output a third result information when the area characteristic falls within the area distribution range limit and the fluctuating value of the area characteristic is less than the second preset value. The control module 46 can be used to command a CPR instrument 47 to increase the compression depth when the control module 46 has received the first result information, the second result information and the third result information. After the CPR instrument 47 increases the compression depth according to the third result information, the control module 46 can notify the calculation unit for peripheral circulation parameter related to CPR quality 42 to calculate the area characteristic of a single pulse wave, and evaluate whether the calculated area characteristic is maximal. If not, the calculation unit 42 may output a fourth result information to the control module 46, based on which the control module 46 can command the CPR instrument 47 to appropriately increase the compression depth. Otherwise, the calculation unit 42 may output a fifth result information and a third prompt message, based on which the control module 46 can control the CPR instrument 47 to maintain the current compression depth. The third prompt message can be used to inform the user that the test subject has reached an optimal compression state.

In this embodiment, the data acquisition unit 40, the waveform generation unit 41, the calculation unit for peripheral circulation parameter based on pulse oximeter 42, the feedback unit 43, the first prompt unit 44, the second prompt unit 45 and the control module 46 can be integrated into one module or can be separately integrated into multiple modules.

Figure 14:
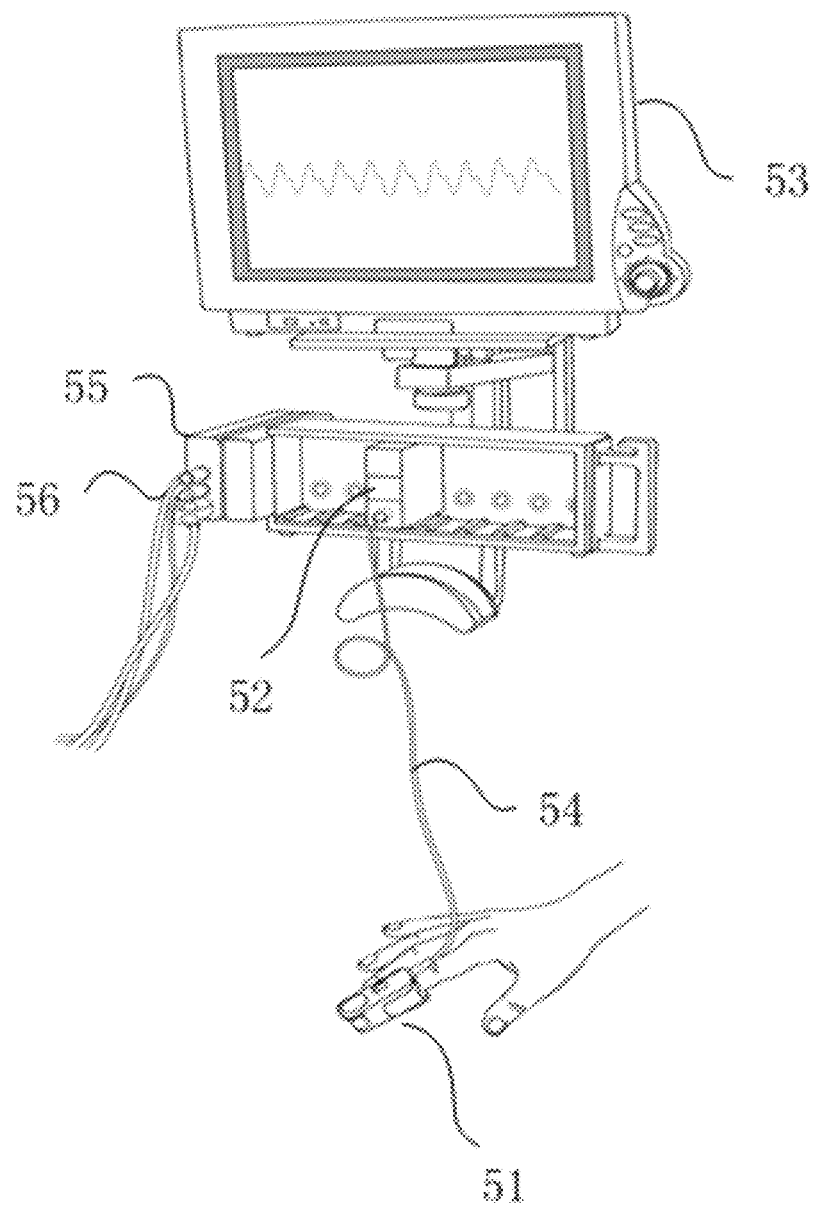
FIG. 14 is a structural diagram of a medical device according to an embodiment of this disclosure.

Based on the above-described methods and/or systems, the embodiments of this disclosure can provide medical devices. As shown in FIG. 14, an example medical device can include a blood oxygen probe 51, a blood oxygen module 52 and an output module 53. Herein the blood oxygen probe 51 can be used to probe a measured position of a test subject and detect blood oxygen signals of the test subject in real time. The blood oxygen module 52 coupled with the blood oxygen probe 51 can be used to acquire the blood oxygen signals outputted by the blood oxygen probe 51, generate a pulse oximetry waveform based on the blood oxygen signals, calculate peripheral circulation parameters related to CPR quality based on the pulse oximetry waveform, and output relevant information of such parameters. The output module 53 coupled to the blood oxygen module 52 can be used to provide feedback on the relevant information on the parameters outputted by the blood oxygen module 52.

Any suitable probe can be used as the blood oxygen probe 51 as long as such probe can detect the blood oxygen signals. As shown in FIG. 2, the blood oxygen probe 51 can include a light-emitting device 100 and a photoelectric detector 101, which may be oppositely disposed on both sides of the blood oxygen probe 51. To calculate the blood oxygen saturation, the light-emitting device 100 may include a red light-emitting tube and an infrared light-emitting tube. In the process of detection, the light emitted by the light-emitting device 100 may penetrate through the arterial blood vessel at the detection position and reach the photoelectric detector 101, and the photoelectric detector 101 can be used to convert the detected red light or infrared light that has penetrated through the arterial blood vessel to electrical signals and output such electrical signals. When the detected blood oxygen signals are used to evaluate for CPR quality, the signals of red light or infrared light may be used to acquire a waveform. Therefore, the light-emitting device 100 may only include a red light emitting tube or an infrared light emitting tube.

In some embodiments, the blood oxygen module 52 and the blood oxygen probe 51 can be connected through a probe accessory 54, where the probe accessory 54 may be a connecting wire. In some embodiments, the blood oxygen module 52 and the blood oxygen probe 51 can realize a signal connection through wireless communication. For example, wireless communication modules can be respectively mounted on the blood oxygen probe 51 and the blood oxygen module 52.

The blood oxygen module 52 can be used to acquire the blood oxygen signals outputted by the blood oxygen probe 51, generate the pulse oximetry waveform based on the blood oxygen signals, and calculate the peripheral circulation parameters related to CPR quality based on the pulse oximetry waveform by using the above-described methods and/or systems. The peripheral circulation parameters related to CPR quality can include the blood oxygen frequency characteristic of the pulse oximetry waveform and the peripheral circulation parameters generated by compression. The peripheral circulation parameters generated by compression can include the amplitude characteristic of a single pulse wave and/or the area characteristic of a single pulse wave. The amplitude characteristic of a single pulse wave can be an absolute amplitude value or an amplitude index, while the area characteristic of a single pulse wave can be an absolute area value or an area index.

In the embodiments of this disclosure, the output module 53 can be used to output various associated information reflecting the peripheral circulation relevant parameters. The associated information may include but is not limited to video information, audio information and light information. The video information can include but is not limited to the trend chart reflecting the dynamic variations of the peripheral circulation relevant parameters, the target range information of the peripheral circulation relevant parameters related to the standard CPR quality, the first alarm message when the peripheral circulation relevant parameters exceed their target range, as well as the second warning information when the dynamic variations of the peripheral circulation relevant parameters exceed their acceptable range of variation. The audio information mainly refers to the auditory sense based on sound variation, including but not limited to parameter value information, parameter variation tendency information, warning prompt message, current compression quality and compression adjustment prompt. These data can be conveyed through either/both a lighted prompt or an audible sound playing the function of a prompt. The light information herein refers to the visual sense based on light variation. It can be a flashing light when the peripheral circulation parameter information exceeds the target range or the stability is too low. It can also be indicated using lamps of different colors to indicate the current compression quality by color change.

In an embodiment, the output module 53 can be designed as a sound playing module. When the data outputted by the blood oxygen module 52 is the audio information related to the peripheral circulation parameters related to CPR quality, the sound playing module can output this data audibly. For example, the output module 53 can notify the user of the current compression state in the form of sound.

In an embodiment, the output module 53 can also be a display module. When the data outputted by the blood oxygen module 52 is the video information related to the peripheral circulation parameters related to CPR quality, the display module can display the video information related to these parameters in visual mode on the display interface. The video information can be displayed in the form of text or image, such as waveform graph.

In an embodiment, the blood oxygen module 52 can separate out the constant component and the fluctuant component from the pulse oximetry waveform, calculate the amplitude characteristic and the area characteristic of a single pulse wave based on the fluctuant component of the pulse oximetry waveform, and calculate the blood oxygen characteristic based on the pulse oximetry waveform or based on the fluctuant component of the pulse oximetry waveform. The blood oxygen characteristic, the amplitude characteristic, the area characteristic as well as some associated data can be processed into video information and further outputted to the display module, where the blood oxygen characteristic may be displayed in the mode of text in real time, the amplitude characteristic and the area characteristic displayed in the mode of waveform graph in real time, while the amplitude distribution range limit and the area distribution range limit (related to the standard values of cardiac compression depth) respectively displayed on the waveform graphs of the amplitude characteristic and the area characteristic. The user may evaluate whether the compression quality has reached the standard by observing the values of the blood oxygen characteristic, the amplitude characteristic and the area characteristic displayed in real time as well as the fluctuation conditions of the amplitude characteristic and the area characteristic. The blood oxygen module 52 can also be used to respectively calculate the fluctuating values of the amplitude characteristic and the area characteristic. When the fluctuating value is less than the preset threshold, the system may output the corresponding prompt message so that the evaluation result can be more accurate and visual.

In an embodiment, the blood oxygen module 52 can operate to recognize the fluctuant components and the constant components in the acquired blood oxygen signals and generate the pulse waveform based on the separated fluctuant components. In an embodiment, the blood oxygen module 52 may also operate to calculate/count the duration of a disappearing period of the pulse wave and/or a total time percentage of the disappearing period of the pulse wave. The total time percentage of the disappearing period of the pulse wave may refer to a ratio between the accumulated duration of the disappearing period of the pulse wave and the duration of the CPR operation. In an embodiment, the blood oxygen module 52 may further operate to calculate/count the duration of an appearing period of the pulse wave and/or a total time percentage of the appearing period of the pulse wave. Here, the appearing period of the pulse wave refers to a duration in which the pulse wave can be generated and/or detected. Alternatively, such an appearing period can be determined by subtracting the disappearing duration from the CPR duration.

In an embodiment, the blood oxygen module 52 may also preset a first threshold and a second threshold, and prompt warning information when the disappearing duration exceeds the first threshold and/or when the total time percentage exceeds the second threshold.

In an embodiment, the blood oxygen module 52 can calculate the total time percentage of the disappearing period of the pulse wave by the following formula:

$$\text{Interval}_{Ratio}^{CPR} = \frac{\sum_{p=1}^{P}\sum_{q=1}^{Q}\text{Interval}(p,q)}{\sum_{n=1}^{N}CPR_{course}(n)} * 100\% \quad (15)$$

where $\sum_{n=1}^{N} CPR_{course}(n)$ represents an accumulated sampling point count during manual/mechanical compression, and $$\sum_{p=1}^{P}\sum_{q=1}^{Q}\text{Interval}(p,q)$$

represents an accumulated sampling point count within a manual/mechanical compression interruption period present in the manual/mechanical compression process (p=1, 2, 3, ... P, and q=1, 2, 3, ... Q, where p represents a $p^{th}$ manual/mechanical compression interruption period, P represents a total number of the manual/mechanical compression interruption periods present in the manual/mechanical compression process having a length of N points, q represents a $q^{th}$ point during the $p^{th}$ CPR interruption period, and Q represents a total point count of the $p^{th}$ manual/mechanical compression interruption period).

In an embodiment, the blood oxygen module 52 can calculate the total time percentage of compression duration (Compression$_{Ratio}^{CPR}$) by: $1-\text{Interval}_{Ratio}^{CPR}$.

In an embodiment, the blood oxygen module 52 can use a plurality of single pulse waves to recognize the disappearing period based on the variations of the multiple pulse waves. In an embodiment, the blood oxygen module 52 can extract about three continuous single pulse waves and recognize the disappearing period of the pulse wave based on an area variation and a shape variation of the multiple single pulse waves.

In addition to providing feedback on the CPR quality by using the peripheral circulation parameters related to CPR quality, the medical device described herein can also be connected with another medical device so as to improve the accuracy of the interaction between that another medical device and the test subject. In such case, the medical device can also include an interaction control interface to make data communication with the other medical device. Through this interaction control interface, the user may further control the automatic switch-over of the functional modes of that another medical device. Specifically, the blood oxygen module 52 can evaluate the current CPR quality according to whether the calculated parameter values of the peripheral circulation parameters are reaching the preset standard and whether the fluctuating values are exceeding the corresponding preset value. It can then further adjust the configuration and the output of that another medical device according to the evaluation result. The adjusted configuration and output can include but are not limited to compression time phase, compression depth (force) and compression frequency performed on the test subject. The adjusted configuration and output can also include keeping the current compression state and increasing the compression depth (force). The fact that these configurations adjust according to the peripheral circulation parameters related to CPR quality may enable the other medical device to perform more accurately on the test subject.

In an embodiment, the interaction control interface can make the connected medical device, and the interaction control interface can be a CPR instrument interface. When the CPR instrument is connected, the CPR instrument may be properly controlled according to the feedback condition so that the CPR instrument can operate at an acceptable state for the resuscitation of the test subject. The detailed description on the control method will be given as follows.

(See FIG. 14) The medical device may also include a control module 55 and a CPR instrument interface 56, where the control module 55 can respectively have a signal connection with the CPR instrument interface 56 and the blood oxygen module 52. When the CPR instrument is designed for automatic regulation of the compression state, the CPR instrument can be connected through the CPR instrument interface 56, and the control module 55 can communicate with the CPR instrument through the CPR instrument interface 56. For example, the control module 55 can receive the information transmitted from the CPR instrument and control the compression frequency and the compression depth of the CPR instrument according to an initial default setting or the feedback information from the blood oxygen module 52.

At the beginning of CPR, the control module 55 can notify the CPR instrument to start operation according to the default compression frequency and compression depth. While the CPR instrument is working, the blood oxygen probe 51 can be used to detect the blood oxygen signals of the test subject, and the blood oxygen module 52 can be used to calculate the blood oxygen characteristic, the amplitude characteristic, and the area characteristic of a single pulse wave based on the blood oxygen signals. In this process, the blood oxygen module 52 may further operate to calculate the fluctuating values of the amplitude characteristic and the area characteristic, evaluate whether the fluctuating value of the amplitude characteristic is less than the first preset value and whether the amplitude characteristic falls within the amplitude distribution range limit, and evaluate whether the fluctuating value of the area characteristic is less than the second preset value and whether the area characteristic falls within the area distribution range limit. If the fluctuating value of the amplitude characteristic is less than the first preset value but the amplitude characteristic does not fall within the amplitude distribution range limit, the blood oxygen module 52 may output the first result information to the control module 55, and then the control module 55 can command the CPR instrument to increase the compression depth according to the first result information. If the fluctuating value of the area characteristic is less than the second preset value but the area characteristic does not fall within the area distribution range limit, the blood oxygen module 52 may output the second result information to the control module 55, and the control module 55 can, according to the second result information, control the CPR instrument to increase the compression depth. If the area characteristic falls within the distribution range limit and the fluctuating value of the area characteristic is less than the second preset value, the blood oxygen module 52 may output the third result information to the control module 55, and the control module 55 can control the CPR instrument to increase the compression depth according to the third result information. The information of increasing the compression depth can then be provided to the blood oxygen module 52, which may calculate the area characteristic of a single pulse wave after increasing the compression depth, and, based on this feedback, evaluate whether the area characteristic of single pulse wave after increasing the compression depth is at its maximal value. If not, the system may output the fourth result information; otherwise, the system can output the fifth result information. The control module 55 can notify the CPR instrument to increase the compression depth according to the fourth result information, or control the CPR instrument to maintain the current compression depth according to the fifth result information.

In clinical applications, the medical device can be a typical bedside equipment such as a patient monitor, defibrillator and electrocardiograph. A blood oxygen module can be added onto the existing bedside equipment. The blood oxygen module can be an independent module or a circuit integrated into the bedside equipment. The functions of the blood oxygen module can be realized by any of the afore-described methods and/or systems through a computer executable program. The display module of the bedside equipment can be used as the output module, and the host of the bedside equipment can be used as the control module, or the control module can be integrated into the host of the bedside equipment.

Figure 15:
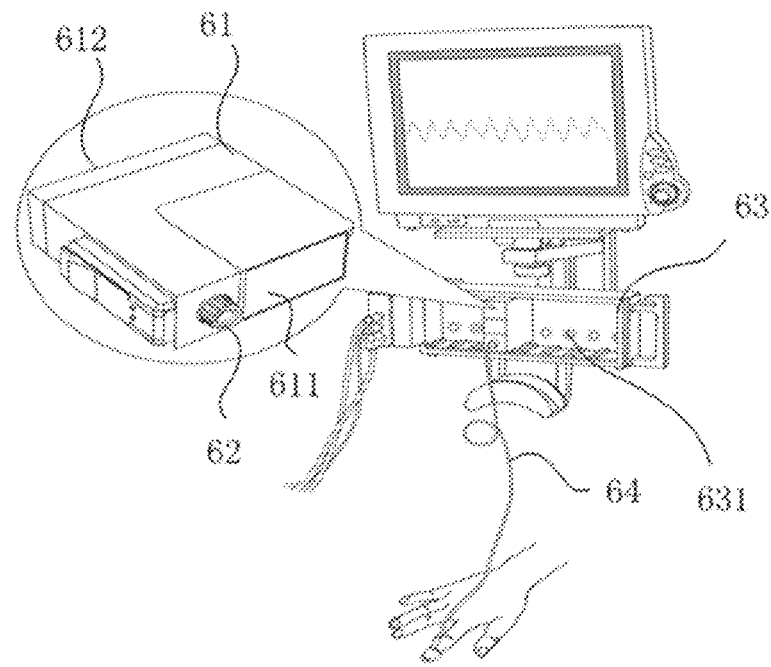
FIG. 15 is a structural diagram of a pulse oximeter plug-in according to an embodiment of this disclosure.

This embodiment discloses a pulse oximeter plug-in that can be used in coordination with the bedside equipment to give real-time feedback of CPR implementation quality. As shown in FIG. 15, the pulse oximeter plug-in can include an enclosure 61, a blood oxygen signal interface 62, a blood oxygen module (not shown in this figure) and an output interface (not shown in this figure). The enclosure 61 may have a user oriented panel 611 and a back panel 612 in contact with the host. The blood oxygen signal interface 62 may be positioned on the panel 611 of the enclosure 61 and used to connect with accessory/device 64 of the blood oxygen probe. The output interface can be positioned on the back panel 612 of the enclosure and used to contact with a corresponding interface 631 on the host. In an embodiment, the output interface can be a conductive contact or a plug port. The blood oxygen module may be located in the enclosure 61. The blood oxygen module can be connected to the blood oxygen signal interface 62 and the output interface, and may communicate with the host through the output interface. The blood oxygen module can be used to receive the blood oxygen signals from the blood oxygen signal interface 62, generate the pulse oximetry waveform based on the blood oxygen signals, calculate the peripheral circulation parameters related to CPR quality based on the pulse oximetry waveform, and output the relevant information of the parameters. The host 63 is positioned in the bedside equipment. In any of the above-described methods and/or systems, the blood oxygen module can process the blood oxygen data and transmit the data to the host, and then the host may display the data through the display module of the bedside equipment for presenting of the CPR implementation quality to the user.

In an embodiment, the relevant information outputted by the blood oxygen module on the peripheral circulation parameters related to CPR quality may include video information, where the video information can include the waveform data of the amplitude characteristic or the waveform data of the area characteristic. The waveform data of the amplitude characteristic may include the amplitude distribution range limit related to the standard value of cardiac compression depth, and the waveform data of the area characteristic may include the area distribution range limit related to the standard value of cardiac compression depth. The blood oxygen module can also be used to calculate the fluctuating value of the amplitude characteristic, and evaluate whether the fluctuating value of the amplitude characteristic is less than the first preset value and whether the amplitude characteristic falls within the amplitude distribution range limit. If so, the system may output the first prompt message, where the first prompt message can be used to inform the user that the current compression depth has reached the standard or determined limit. If the blood oxygen module evaluates that the fluctuating value of the amplitude characteristic is less than the first preset value but the amplitude characteristic does not fall within the amplitude distribution range limit, the system may output the first result information, where the first result information can be used to command the CPR instrument to increase the compression depth. The blood oxygen module can also be used to calculate the fluctuating value of the area characteristic, evaluate whether the fluctuating value of the area characteristic is less than the second preset value and whether the area characteristic falls within the area distribution range limit. If so, the system may output the second prompt message, where the second prompt message can be used to inform the user that the current compression quality has reached the standard. If the blood oxygen module evaluates that the fluctuating value of the area characteristic is less than the second preset value but the area characteristic does not fall within the area distribution range limit, the system may output the second result information, which can be used to command the CPR instrument to increase the compression depth.

Figure 16:
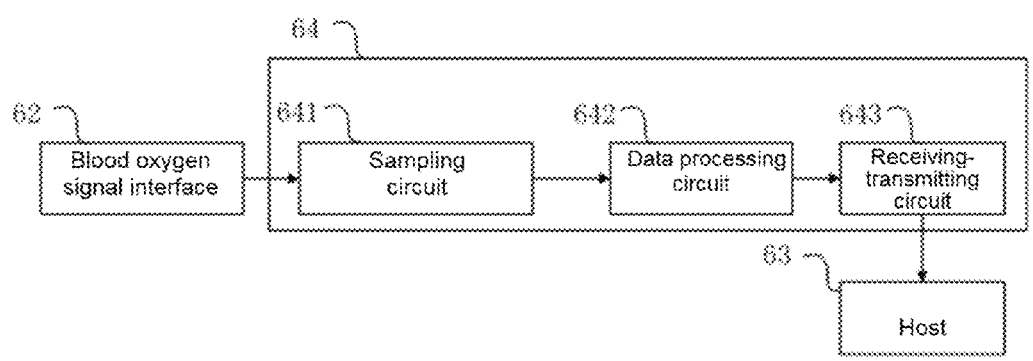
FIG. 16 is a block diagram of a blood oxygen module according to an embodiment of this disclosure.

In an embodiment, the blood oxygen module/device/accessory 64 can have the structure as shown in FIG. 16 and include a sampling circuit 641, a data processing circuit 642 and a receiving-transmitting circuit 643. The sampling circuit 641 can be coupled to the blood oxygen signal interface 62 and be used to take samples of the blood oxygen signals inputted by the blood oxygen signal interface 62. The data processing circuit 642 may function as the blood oxygen module and can be coupled to the output-end of the sampling circuit 641. The data processing circuit 642 may be used to generate the pulse oximetry waveform based on the sampled blood oxygen signals, calculate the peripheral circulation parameters related to the CPR quality based on the pulse oximetry waveform, and output the information related to these parameters after data processing. In this embodiment, the data processing circuit 642 can be a microprocessor MCU, and its functions can be realized by a computer executable program. The receiving-transmitting circuit 643 can be connected between the data processing circuit 642 and the output interface, and used to achieve the communication between the data processing circuit 642 and the host 63 through the output interface. The blood oxygen module 64 may also include some peripheral circuits, such as the amplifying circuit to amplify the sampled signals and/or the filtering circuit to filter the sampled signals. The peripheral circuits may also include a voltage stabilizing circuit, where the voltage stabilizing circuit can be used to receive power from the host through the output interface and then provide electric power for each part of the circuits after voltage regulation.

In an embodiment, the pulse oximeter plug-in can realize wireless communication with the host. For example, the receiving-transmitting circuit 643 may include a wireless communication module, and the host may also include a wireless communication module, so that the communication between the pulse oximeter plug-in and the host can be wirelessly achieved. In this embodiment, the pulse oximeter plug-in has no need for the output interface, and it has no need to directly contact the host either, which means it can be placed apart from the host.

In an embodiment, a medical equipment may include an optical transceiver, a digital processor and an output module. The optical transceiver can include a light emitting tube and a receiving tube, where the light emitting tube can emit at least one light signal to penetrate through human tissue, and the receiving tube can receive the at least one light signal and convert the at least one light signal into at least one electrical signal. The digital processor can convert the at least one electrical signal into at least one digital signal and process the at least one digital signal to obtain peripheral circulation relevant parameters. Based on the signal processing, the digital processor can further recognize a pulse wave and count duration of a disappearing period of the pulse wave. The output module can output associated information corresponding to the peripheral circulation relevant parameters and the counting information.

In an embodiment, the digital processor can recognize the pulse wave by recognizing real-time pulsatile perfusion characteristic reflected by the digital signal. In an embodiment, the digital processor can obtain the real-time pulsatile perfusion characteristic reflected by the digital signal by identifying fluctuant components and constant components in the at least one digital signal.

In an embodiment, the counting information may include the disappearing duration of the pulse wave. In another embodiment, the counting information may also include the appearing duration of the pulse wave, i.e. the continuous compression period during CPR operation. The output module can be a display interface, and the disappearing duration of the pulse wave can be displayed on the display interface. In another embodiment, the counting information may also include a total time percentage of the disappearing period of the pulse wave, which may refer to a ratio between an accumulated duration of the disappearing period of the pulse wave and duration of the CPR operation. The display interface may also display the total time percentage of the disappearing period of the pulse wave. The digital processor may also preset a first threshold and a second threshold, and prompt warning information when the disappearing duration exceeds the first threshold and/or when the total time percentage exceeds the second threshold.

In a case of cardiac arrest for any patient in or outside a hospital, medical staff can immediately connect the patient to a monitor during emergency treatment, so as to display the heart rate, blood pressure, respiration and pulse oximeter saturation of the patient. For the patient in cardiac arrest, an effective first aid method is high-quality CPR of which a factor is high-quality chest compression. Clinically, the parameters for evaluating the compression quality may include compression position, compression frequency, compression depth, compression-relaxation time proportion and thorax rebound condition. In the case of incorrect compression position, insufficient depth, too high/low frequency and/or insufficient relaxation, the CPR quality can be affected. The embodiments of this disclosure may find such variation and the provide feedback to the medical staff regarding the CPR implementation quality in real-time by using the peripheral circulation parameters calculated based on a pulse oximetry waveform. Furthermore, the systems are also non-invasive to the patient. When the systems are used in coordination with an automatic resuscitator, the control on the automatic resuscitator can be realized according to the feedback information. In emergency treatment, the blood oxygen saturation of the patient is often detected to measure the blood oxygen signals of the patient. Therefore, the embodiments of this disclosure generally have no need for additional feedback device, thus being convenient and economical in practice.

The following test results describe the peripheral circulation parameters related to CPR quality that can be calculated according to various embodiments described herein and used for evaluation of CPR implementation quality.

Figure 17:
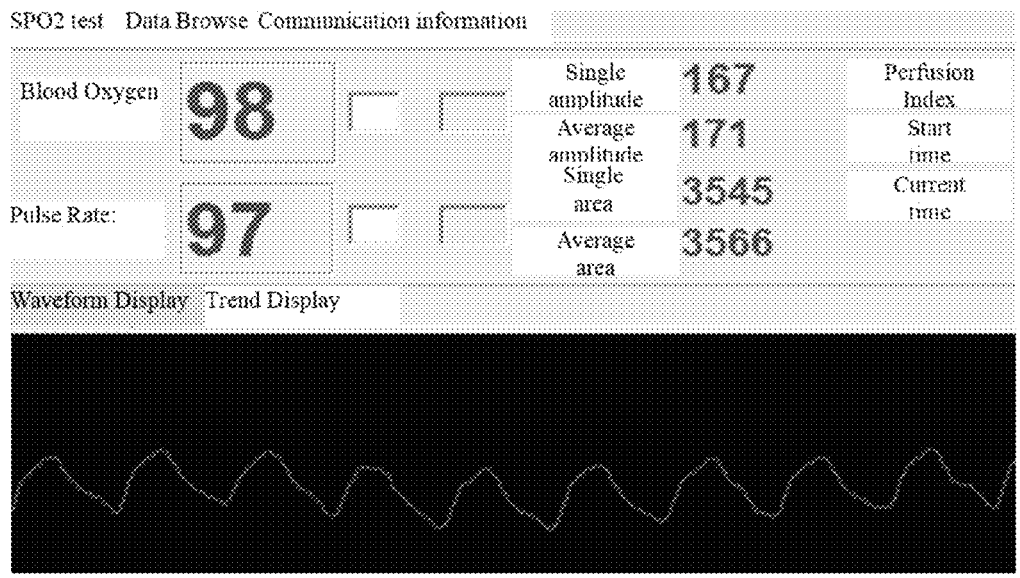
FIG. 17 shows a display interface when spontaneous circulation exists.
Figure 18:
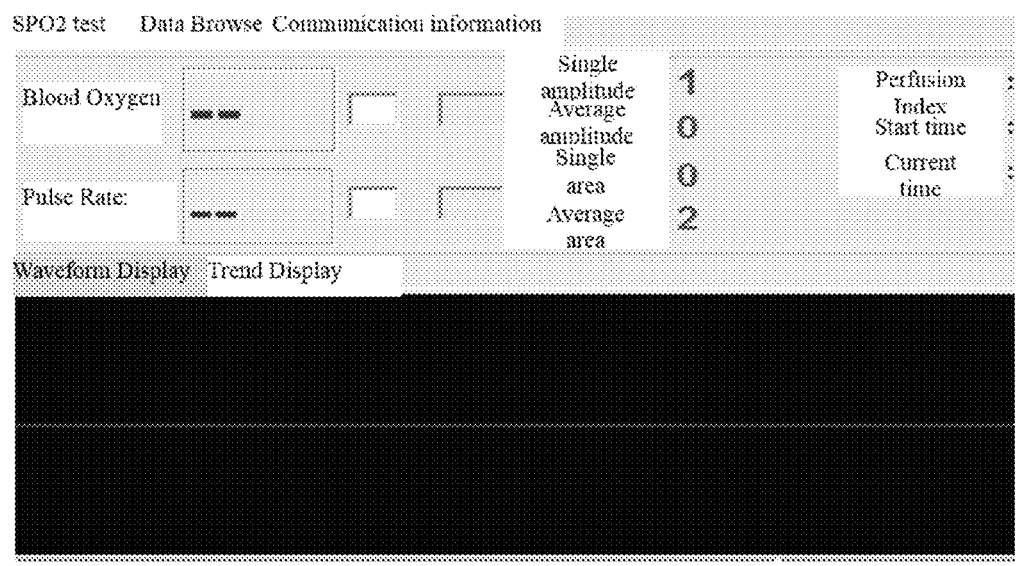
FIG. 18 shows a display interface when spontaneous circulation disappears.
Figure 19:
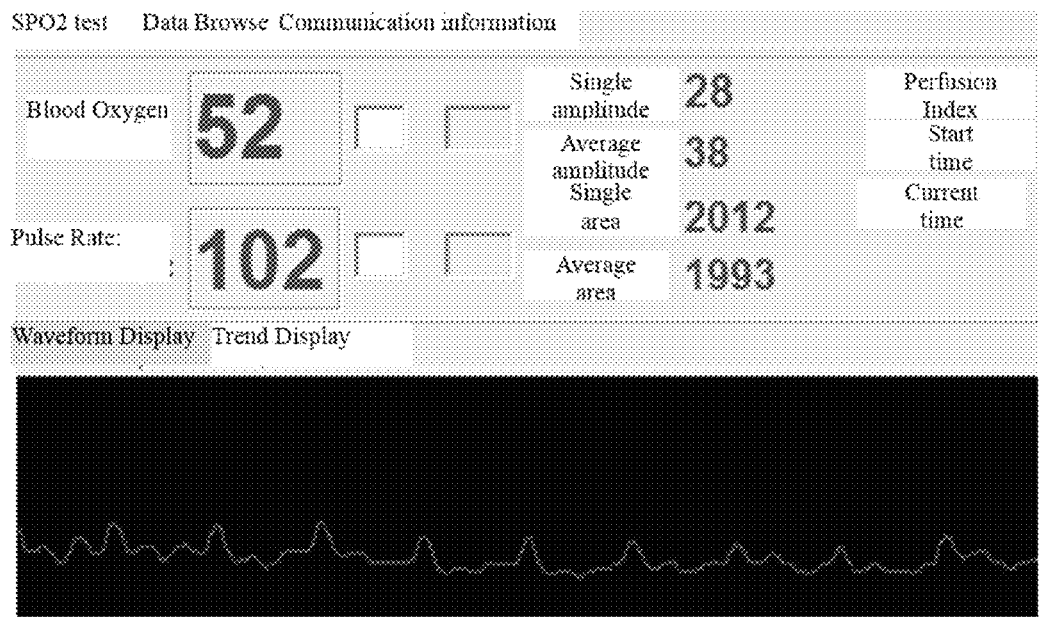
FIG. 19 shows a display interface in a case of low-quality CPR.
Figure 20:
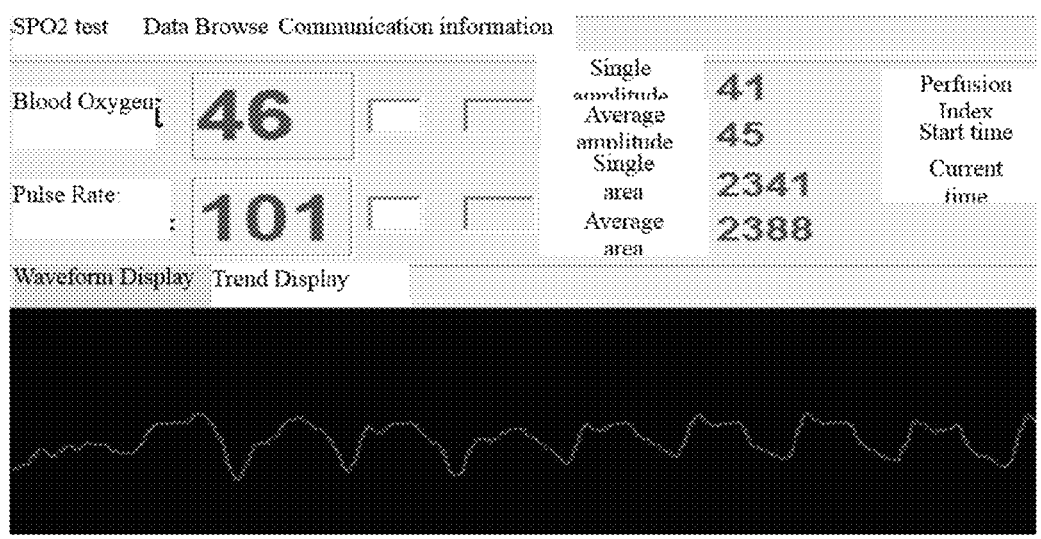
FIG. 20 shows a display interface in a case of medium-quality CPR.
Figure 21:
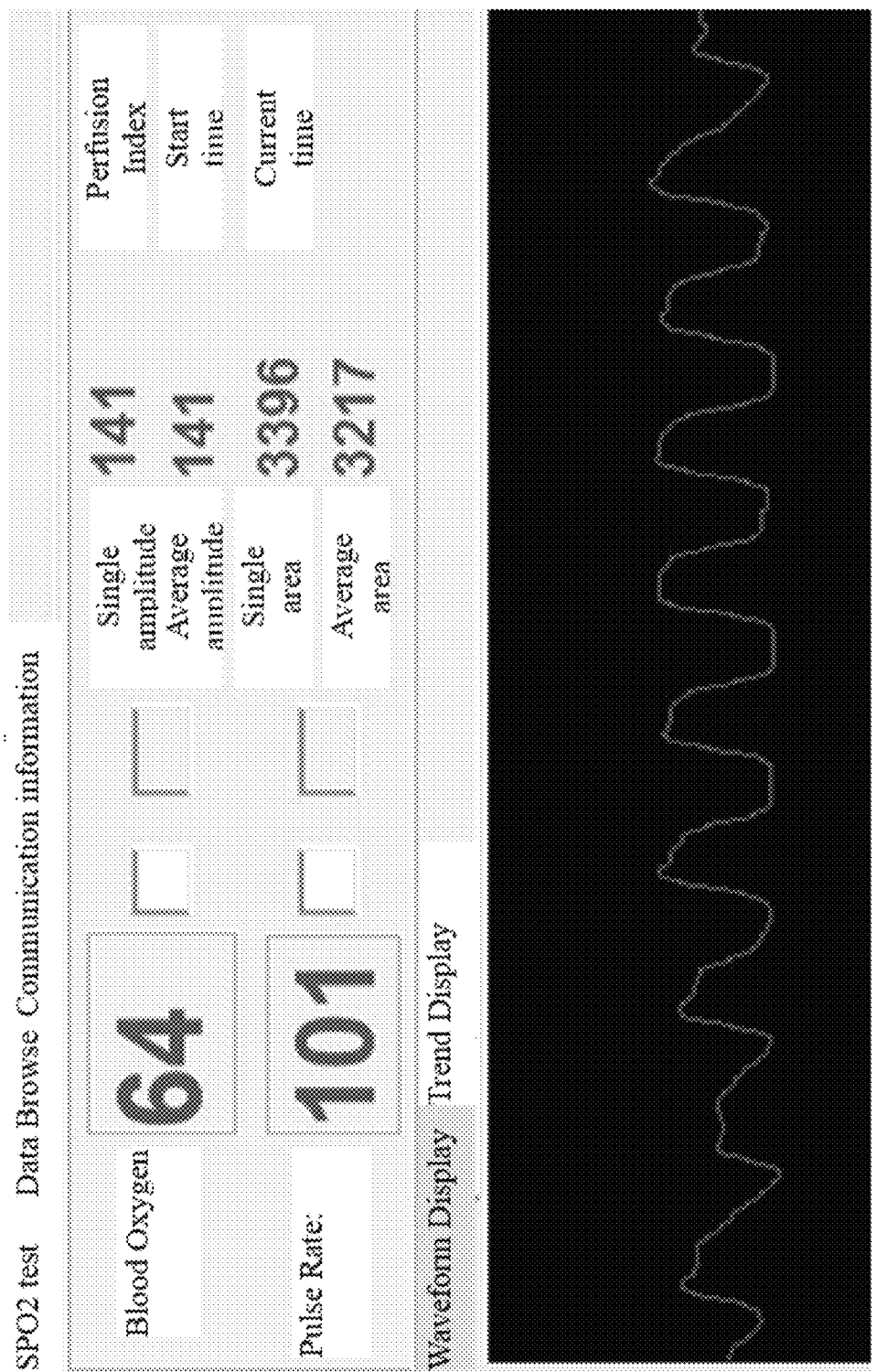
FIG. 21 shows a display interface in a case of high-quality CPR.
Figure 22:
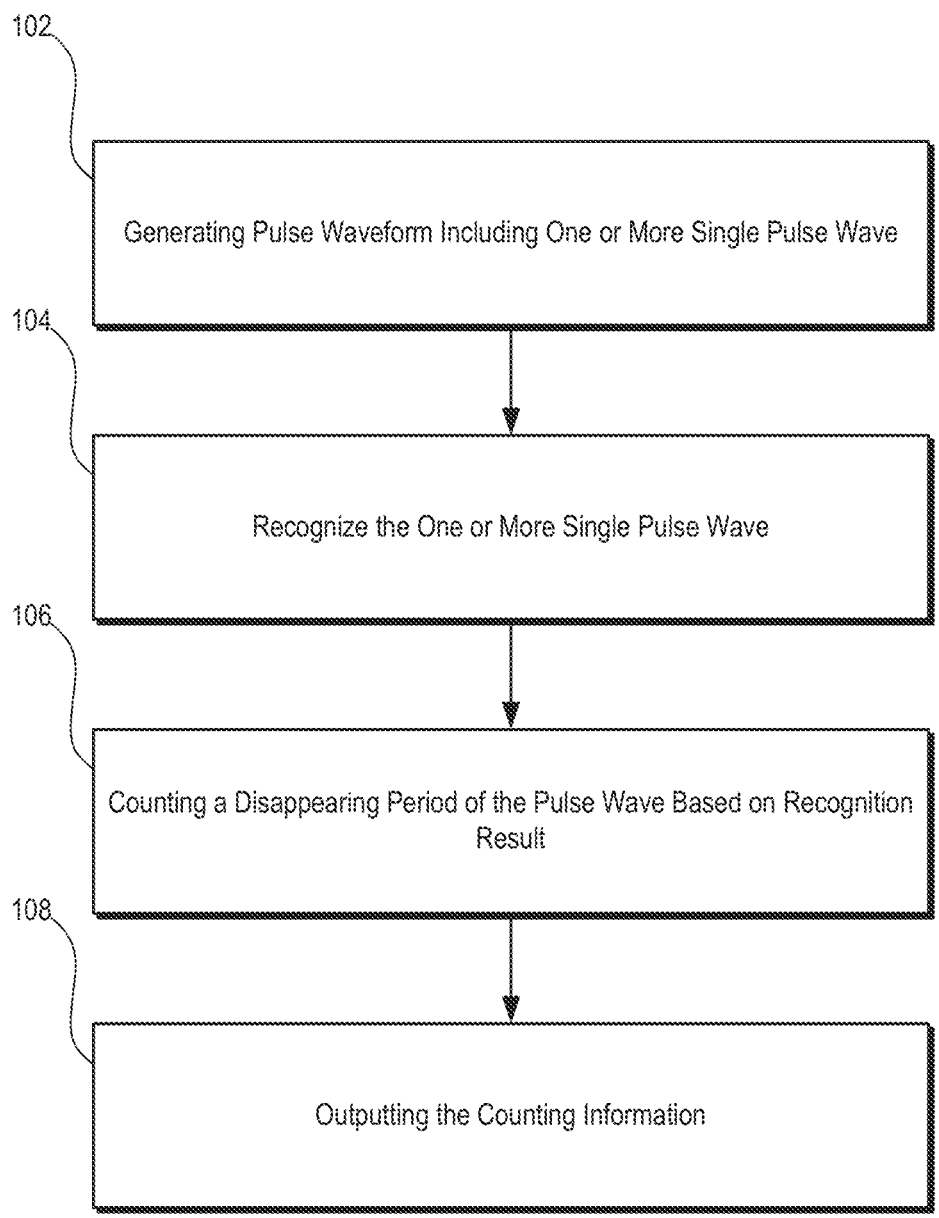
FIG. 22 is a flow chart for monitoring a compression interruption period during the CPR process according to an embodiment of this disclosure.

In animal experiment, the automatic resuscitator is used for chest compression. Two indexes, compression frequency and compression position, are selected herein. According to the compression depth, the CPR implementation quality is divided into high quality (5 cm), medium quality (4 cm) and low quality (3 m). In these three cases, the system outputs the value, the waveform, the amplitude and the area under the curve of pulse oximeter saturation, where the amplitude and the area under the curve include the real-time value and the average value in 30 seconds. The average values with higher reference value are used to reduce error as shown in FIGS. 17-21. As shown in FIG. 17, when the patient has spontaneous circulation, the value of the pulse oximeter saturation is high while the values of the amplitude and the area under the curve are also high. As shown in FIG. 18, when the spontaneous circulation of the patient has disappeared (in case of cardiac arrest), the value of the pulse oximeter saturation cannot be measured, and the values of the amplitude and the area under the curve are displayed as zero or extremely low values. In case of low-quality CPR, the values of such parameters are relatively lower as shown in FIG. 19. In case of medium quality CPR, the values of the amplitude and the area under the curve are higher than those of low-quality CPR as shown in FIG. 20. In case of high-quality CPR, the values of various parameters are higher as shown in FIG. 21.

In practice, if the relevant parameter values outputted in real time are lower than the specified values of high-quality CPR, the resuscitation quality should be enhanced to realize high-quality resuscitation, improve the vital organ perfusion and overall prognosis. The CPR monitoring feedback systems described herein can reflect CPR quality in a real-time, convenient, non-invasive and economical manner, and thus can be widely used and applied to the field of cardiopulmonary resuscitation. For clinicians, this disclosure can provide visual and real-time monitoring feedback indexes to improve CPR quality. Therefore, this disclosure has great practical application value and broad application prospects. Furthermore, it has high social value for the development of health care industry and for improving outcomes in resuscitation for the people.

Those skilled in the art can understand that, all or partial steps of various methods in the embodiments above can be completed by using a program to command relevant hardware products. This program can be stored in a readable storage medium of the computer, and the storage medium may include ROM, RAM, disk or optical disk.

The above content gives further detailed descriptions on this disclosure in combination with specific embodiments. Specific implementations of this disclosure are not limited to these descriptions. For those skilled in the art, various substitutions can be made without deviation from the concept and spirit of this disclosure.

The invention claimed is:

1. A cardio-pulmonary resuscitation (CPR) monitoring device, comprising:
   an optical transceiver comprising:
      a light emitting tube that emits at least one light signal; and
      a receiving tube that receives the at least one light signal after the at least one light signal has passed through human tissue and converts the at least one light signal into at least one electrical signal;
   a digital processor to convert the at least one electrical signal into at least one digital signal including a real-time pulsatile perfusion characteristic and process the at least one digital signal to obtain at least one peripheral circulation parameter related to CPR quality; wherein the digital processor obtains the real-time pulsatile perfusion characteristic by separating fluctuant components and constant components of the at least one digital signal; and, wherein the CPR quality is related to the fluctuant and constant components of the at least one peripheral circulation parameter and conformity of the at least one peripheral circulation parameter with a target range; and
   an output module to output information corresponding to the at least one peripheral circulation parameter.

2. The CPR monitoring device of claim 1, wherein the at least one peripheral circulation parameter includes at least one of: a first reflecting parameter that reflects a frequency variation characteristic of CPR compression, a second reflecting parameter that reflects a depth variation characteristic of CPR compression, and a third reflecting parameter that reflects comprehensive variation characteristics of frequency and depth of CPR compression.

3. The CPR monitoring device of claim 2, wherein
   the digital processor obtains the first reflecting parameter by identifying the fluctuant component of the at least one digital signal and calculating a frequency of the fluctuant component;
   the digital processor obtains the second reflecting parameter by identifying the fluctuant component of the at least one digital signal and making an amplitude conversion on the fluctuant component.

4. The CPR monitoring device of claim 2, wherein
   the digital processor obtains a corrected second reflecting parameter by identifying the fluctuant component and the constant component of the at least one digital signal and calculating an amplitude ratio of the fluctuant component and the constant component after respectively making amplitude conversion on these two components.

5. The CPR monitoring device of claim 2, wherein
   the digital processor obtains the third reflecting parameter by identifying the fluctuant component of the at least one digital signal and calculating an area integral of the fluctuant component.

6. The CPR monitoring device of claim 2, wherein
   the digital processor obtains a corrected third reflecting parameter by identifying the fluctuant component and the constant component of the at least one digital signal and calculating an area ratio between an area integral of the fluctuant component and an area integral of the constant component.

7. The CPR monitoring device of claim 1, wherein the digital processor processes the at least one digital signal using at least one of a time domain analysis method and a frequency domain analysis method.

8. The CPR monitoring device of claim 7, wherein the time domain analysis method calculates the at least one peripheral circulation parameter by identifying at least one of a frequency characteristic, an amplitude characteristic and an area characteristic of the at least one digital signal; and
   wherein the frequency domain analysis method is used for frequency spectrum identification based on non-zero frequency spectrum or used for frequency spectrum identification based on a ratio between non-zero frequency spectrum and zero-frequency spectrum.

9. The CPR monitoring device of claim 8, wherein the time domain analysis method identifies the amplitude characteristic and the area characteristic of the at least one digital signal based on the fluctuant component of the at least one digital signal or based on a ratio between the fluctuant component and a constant component of the at least one digital signal.

10. The CPR monitoring device of claim 1, wherein the CPR monitoring device is configured as a medical device plug-in, the medical device plug-in comprising:
    an enclosure component;
    a physiological signal acquisition interface, which is positioned on an external surface of the enclosure component and is used to be connected with signal acquisition accessories;
    a physiological signal processing module positioned in the enclosure component, wherein the physiological signal processing module is used to obtain acquisition signals through the physiological signal acquisition interface, convert the acquisition signals into digital signals and obtain the at least one peripheral circulation parameter through calculation based on the digital signals;
    an interactive interface, wherein the physiological signal processing module makes information interaction with a host through the interaction interface.

11. A cardio-pulmonary resuscitation (CPR) monitoring device, comprising:
    a blood oxygen probe to probe measured positions of a test subject and to detect blood oxygen signals of the test subject in real time;
    a blood oxygen module coupled to the blood oxygen probe, wherein the blood oxygen module acquires the blood oxygen signals outputted from the blood oxygen probe, generates a pulse oximetry waveform based on the blood oxygen signals, separates a constant component and a fluctuant component of the pulse oximetry waveform, calculates one or more peripheral circulation parameters related to CPR quality based on the pulse oximetry waveform, and outputs associated information on the at least one peripheral circulation parameters related to CPR quality; and
    an output module coupled to the blood oxygen module, wherein the output module provides feedback on the associated information outputted by the blood oxygen module on the one or more peripheral circulation parameters related to CPR quality;
    wherein the at least one peripheral circulation parameters include a blood oxygen frequency characteristic of the pulse oximetry waveform and one or more peripheral circulation parameters generated by compression; and wherein the one or more peripheral circulation parameters generated by compression include amplitude characteristic of a single pulse wave and/or an area characteristic of a single pulse wave.

12. The CPR monitoring device of claim 1, wherein the blood oxygen module calculates the blood oxygen frequency characteristic and the one or more peripheral circulation parameters generated by compression based on one of the fluctuant component of the pulse oximetry waveform and a ratio between the fluctuant component and the constant component of the pulse oximetry waveform.

13. The CPR monitoring device of claim 11, wherein the output module is a display module to display at least one of a waveform graph of the amplitude characteristic and the area characteristic on a display interface; wherein the display module further displays at least one of an amplitude distribution range limit and an area distribution range limit related to a standard value of chest compression quality on the waveform graph of at least one of the amplitude characteristic and the area characteristic.

14. The CPR monitoring device of claim 11, wherein the blood oxygen module also calculates a fluctuating value of the amplitude characteristic, evaluates whether the fluctuating value of the amplitude characteristic is less than a first preset value and whether the amplitude characteristic falls within an amplitude distribution range limit; and if so, the blood oxygen module outputs a first prompt message to inform a user that current compression quality has reached the standard;

or the blood oxygen module also calculates a fluctuating value of the area characteristic, evaluates whether the fluctuating value of the area characteristic is less than a second preset value and whether the area characteristic is within an area distribution range limit; and if so, the blood oxygen module outputs a second prompting message to inform a user that current compression quality has reached the standard.

15. The CPR monitoring device of claim 11, wherein the amplitude characteristic includes an absolute amplitude value or an amplitude index, wherein the amplitude index is a ratio between the absolute amplitude value of single pulse wave of the fluctuant component of an amplified pulse oximetry waveform and corresponding DC component of the amplified pulse oximetry waveform; and wherein the area characteristic includes an absolute area value or an area index, wherein the area index is a ratio between the absolute area value of single pulse wave of the fluctuant component of an amplified pulse oximetry waveform and corresponding DC component of the amplified pulse oximetry waveform.

16. The CPR monitoring device of claim 11, further comprising an interaction control interface which is connected with another medical device to realize data communication therewith;

wherein the blood oxygen module evaluates the current CPR quality based on values and/or fluctuating level of the at least one peripheral circulation parameters, and adjusts configuration and output of said another medical device through the interaction control interface based on evaluation results;

wherein the configuration and output include one or more of compression depth, compression frequency and compression time phase.

17. The CPR monitoring device of claim 16, further comprising:

a control module, wherein the control module is respectively in signal connection with the interaction control interface and the blood oxygen module and is at least used to control the compression frequency and the compression depth of said another medical device;

wherein the blood oxygen module also calculates a fluctuating value of the amplitude characteristic, evaluates whether the fluctuating value of the amplitude characteristic is less than a first preset value and whether the amplitude characteristic falls within an amplitude distribution range limit; if the fluctuating value of the amplitude characteristic is less than the first preset value but the amplitude characteristic does not fall within the amplitude distribution range limit, the blood oxygen module outputs a first result information to the control module, and the control module controls said another medical device to increase the compression depth according to the first result information.

18. The CPR monitoring device of claim 16, further comprising:

a control module, wherein the control module is in communication with the interaction control interface, the blood oxygen module and the output module, and is at least used to control the compression frequency and the compression depth of said another medical device;

wherein the blood oxygen module calculates a fluctuating value of the area characteristic, evaluates whether the fluctuating value of the area characteristic is less than a second preset value and whether the area characteristic falls within an area distribution range limit; if the fluctuating value of the area characteristic is less than the second preset value but the area characteristic does not fall within the area distribution range limit, the blood oxygen module outputs a second result information to the control module, and the control module controls said another medical equipment to increase the compression depth according to the second result information; if the area characteristic falls within the area distribution range limit and the fluctuating value of the area characteristic is less than the second preset value, the blood oxygen module outputs a third result information to the control module, and the control module controls said another medical device to increase the compression depth according to the third result information and provide feedback on increasing the compression depth to the blood oxygen module; based on this feedback, the blood oxygen module calculates the area characteristic of single pulse wave after increasing the compression depth, evaluates whether the area characteristic of single pulse wave after increasing the compression depth is at a maximum value; if not, the blood oxygen module outputs a fourth result information; if so, the blood oxygen module outputs a fifth result information; the control module controls said another medical device to increase the compression depth according to the fourth result information, or controls said another medical device to maintain the current compression depth according to the fifth result information.

19. The CPR monitoring device of claim 11, wherein the blood oxygen module obtains a pulse waveform comprising one or more single pulse waves based on the fluctuant component that are separated from the pulse oximetry waveform, and counts a disappearing period of the pulse wave by evaluating characteristic variation of the one or more pulse waves.

20. The CPR monitoring device of claim 19, wherein the blood oxygen module counts at least one of a duration of the disappearing period of the one or more pulse waves and a total time percentage of the disappearing period of the pulse wave;

or the blood oxygen module is also capable of counting a compression period in which the pulse wave is generated; wherein the blood oxygen module counts duration of the disappearing period of the pulse wave and/or a total time percentage of the disappearing period of the pulse wave, and counts duration of the compression period and/or a total time percentage of the compression period.

21. The CPR monitoring device of claim 20, wherein the blood oxygen module presets a first threshold, a second threshold and a third threshold, and prompts warning information when the duration of the disappearing period of the pulse wave is larger than the first threshold, when the total time percentage of the disappearing period of the pulse wave is larger than the second threshold, and/or when the total time percentage of the compression period is smaller than the third threshold.

22. A cardio-pulmonary resuscitation (CPR) monitoring device, comprising:

an optical transceiver, comprising:
  a light emitting tube that emits at least one light signal; and
  a receiving tube that receives the at least one light signal after the at least one light signal has passed through human tissue and converts the at least one light signal into at least one electrical signal;
a digital processor to convert the at least one electrical signal into at least one digital signal including a real-time pulsatile perfusion characteristic and process the at least one digital signal to obtain at least one peripheral circulation parameter related to CPR quality; wherein the digital processor processes the at least one digital signal using a frequency domain analysis method to separate a zero-frequency spectrum and a non-zero frequency spectrum; and
an output module to output CPR quality information corresponding to the at least one peripheral circulation parameter.

23. The CPR monitoring device of claim 22, wherein the frequency domain analysis method is used for frequency spectrum identification based on the separated non-zero frequency spectrum or used for frequency spectrum identification based on a ratio between the separated non-zero frequency spectrum and zero-frequency spectrum.

24. A cardio-pulmonary resuscitation (CPR) monitoring device, comprising:

an optical transceiver comprising:
  a light emitting tube that emits at least one light signal; and
  a receiving tube that receives the at least one light signal after the at least one light signal has passed through human tissue and converts the at least one light signal into at least one electrical signal;
a digital processor to convert the at least one electrical signal into at least one digital signal including a real-time pulsatile perfusion characteristic and process the at least one digital signal to obtain at least one peripheral circulation parameter related to CPR quality; wherein the at least one peripheral circulation parameter includes at least one of: a first reflecting parameter that reflects a frequency variation characteristic of CPR compression, a second reflecting parameter that reflects a depth variation characteristic of CPR compression, and a third reflecting parameter that reflects comprehensive variation characteristics of frequency and depth of CPR compression; wherein the digital processor obtains the real-time pulsatile perfusion characteristic by separating fluctuant components and constant components of the at least one digital signal; and wherein the digital processor obtains a corrected second reflecting parameter by identifying the fluctuant components and the constant components of the at least one digital signal and calculating an amplitude ratio of the fluctuant components and the constant components after respectively making amplitude conversion on these two components; and
an output module to output information corresponding to the at least one peripheral circulation parameter.

25. A cardio-pulmonary resuscitation (CPR) monitoring device, comprising:

an optical transceiver comprising:
  a light emitting tube that emits at least one light signal; and
  a receiving tube that receives the at least one light signal after the at least one light signal has passed through human tissue and converts the at least one light signal into at least one electrical signal;
a digital processor to convert the at least one electrical signal into at least one digital signal including a real-time pulsatile perfusion characteristic and process the at least one digital signal to obtain at least one peripheral circulation parameter related to CPR quality; wherein the at least one peripheral circulation parameter includes at least one of: a first reflecting parameter that reflects a frequency variation characteristic of CPR compression, a second reflecting parameter that reflects a depth variation characteristic of CPR compression, and a third reflecting parameter that reflects comprehensive variation characteristics of frequency and depth of CPR compression; wherein the digital processor obtains the real-time pulsatile perfusion characteristic by separating fluctuant components and constant components of the at least one digital signal; and wherein the digital processor obtains a corrected third reflecting parameter by identifying the fluctuant components and the constant components of the at least one digital signal and calculating an area ratio between an area integral of the fluctuant components and an area integral of the constant components; and
an output module to output information corresponding to the at least one peripheral circulation parameter.

* * * * *